United States Patent
Jensen et al.

(10) Patent No.: US 10,176,821 B2
(45) Date of Patent: Jan. 8, 2019

(54) MONAURAL INTRUSIVE SPEECH INTELLIGIBILITY PREDICTOR UNIT, A HEARING AID AND A BINAURAL HEARING AID SYSTEM

(71) Applicant: Oticon A/S, Smørum (DK)

(72) Inventors: Jesper Jensen, Smørum (DK); Jan Mark De Haan, Smørum (DK); Asger Heidemann Andersen, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 15/445,472

(22) Filed: Feb. 28, 2017

(65) Prior Publication Data

US 2017/0256269 A1 Sep. 7, 2017

(30) Foreign Application Priority Data

Mar. 1, 2016 (EP) .................................... 16157993

(51) Int. Cl.
*G10L 21/02* (2013.01)
*G10L 21/0232* (2013.01)
(Continued)

(52) U.S. Cl.
CPC .......... *G10L 21/0205* (2013.01); *A61N 1/378* (2013.01); *G10L 21/0232* (2013.01);
(Continued)

(58) Field of Classification Search
None
See application file for complete search history.

(56) References Cited

U.S. PATENT DOCUMENTS

| 2011/0224976 | A1* | 9/2011 | Taal | G10L 25/69 704/205 |
| 2013/0051566 | A1* | 2/2013 | Pontoppidan | H04R 25/353 381/23.1 |

(Continued)

OTHER PUBLICATIONS

Chen, "The relative importance of temporal envelope information for intelligibility prediction: A study on cochlear-implant vocoded speech", Medical Engineering & Physics, vol. 33, 2011, pp. 1033-1038.

(Continued)

*Primary Examiner* — Curtis Kuntz
*Assistant Examiner* — Qin Zhu
(74) *Attorney, Agent, or Firm* — Birch, Stewart, Kolasch & Birch, LLP

(57) ABSTRACT

A monaural intrusive speech intelligibility predictor unit comprises: first and second input units for providing time-frequency representations s(k,m) and x(k,m) of noise-free and noisy and/or processed versions of a target signal, respectively, k being a frequency bin index, k=1, 2, . . . , K, and m being a time index; first and second envelope extraction units for providing time-frequency sub-band representations of the signals $s_j(m)$ and $x_j(m)$, j being a frequency sub-band index, j=1, 2, . . . , J; first and second time-frequency segment division units for dividing the time-frequency sub-band representations $s_j(m)$ and $x_j(m)$ into time-frequency segments $S_m$ and $X_m$ corresponding to a number N of successive samples of the sub-band signals; an intermediate speech intelligibility calculation unit adapted for providing intermediate speech intelligibility coefficients $d_m$ estimating an intelligibility of said time-frequency segment $X_m$, based on said time-frequency segments $S_m$ and $X_m$ or normalized and/or transformed versions $\tilde{S}_m$, and $\tilde{X}_m$ thereof; and a final monaural speech intelligibility calculation unit for calculating a final monaural speech intelligi- (Continued)

bility predictor d estimating an intelligibility of said noisy and/or processed version x of the target signal by combining said intermediate speech intelligibility coefficients $d_m$, or a transformed version thereof, over time. A hearing aid comprises a monaural, intrusive intelligibility predictor unit, and a configurable signal processor adapted to control or influence the processing of one or more electric input signals representing environment sound to maximize the final speech intelligibility predictor d. A binaural hearing aid system comprises first and second hearing aids.

19 Claims, 8 Drawing Sheets

(51) Int. Cl.
| | |
|---|---|
| *G10L 21/038* | (2013.01) |
| *G10L 25/06* | (2013.01) |
| *G10L 25/60* | (2013.01) |
| *A61N 1/378* | (2006.01) |
| *H04R 25/00* | (2006.01) |

(52) U.S. Cl.
CPC ............ *G10L 21/038* (2013.01); *G10L 25/06* (2013.01); *G10L 25/60* (2013.01); *H04R 25/505* (2013.01); *H04R 25/552* (2013.01); *H04R 25/554* (2013.01); *H04R 25/70* (2013.01); *H04R 25/558* (2013.01); *H04R 25/606* (2013.01); *H04R 2225/025* (2013.01); *H04R 2225/41* (2013.01); *H04R 2225/43* (2013.01); *H04R 2225/55* (2013.01)

(56) References Cited

U.S. PATENT DOCUMENTS

| | | | |
|---|---|---|---|
| 2015/0019213 A1* | 1/2015 | Nongpiur | G10L 21/0364 704/225 |
| 2015/0289065 A1* | 10/2015 | Jensen | H04R 25/552 381/315 |
| 2016/0234610 A1* | 8/2016 | Jensen | H04R 25/552 |
| 2017/0125033 A1* | 5/2017 | Kjems | G10L 21/0232 |

OTHER PUBLICATIONS

Jensen et al., "Prediction of Intelligibility of Noisy and Time-Frequency Weighted Speech based on Mutual Information Between Amplitude Envelops", INTERSPEECH 2013, Aug. 25-29, 2013, pp. 1174-1178.

Taghia et al., "On Mutual Information as a Measure of Speech Intelligibility", 2012 IEEE International conference on Acoustics, Speech and Signal Processing (ICASSP 2012), Mar. 25, 2012, pp. 65-68.

Tang et al., "Evaluating the predictions of objective intelligibility metrics for modified and synthetic speech", Computer Speech and Language, vol. 35, 2016, pp. 73-92.

* cited by examiner

US 10,176,821 B2

MONAURAL INTRUSIVE SPEECH INTELLIGIBILITY PREDICTOR UNIT, A HEARING AID AND A BINAURAL HEARING AID SYSTEM

SUMMARY

The present disclosure deals with monaural, intrusive intelligibility prediction of noisy/processed speech signals comprising a target signal component based on simultaneous knowledge of a substantially noise-free ('clean') version of the target signal component. The present disclosure further relates to a hearing aid comprising a monaural, intrusive intelligibility predictor unit, and to a binaural hearing aid system comprising first and second hearing aids, each comprising a monaural, intrusive intelligibility predictor unit, wherein the binaural hearing aid system is configured to establish a wireless link allowing the exchange of monaural speech intelligibility predictors or information derived therefrom between the first and second hearing aids.

A Monaural Speech Intelligibility Predictor Unit:

In an aspect of the present application provides a monaural speech intelligibility predictor unit adapted for receiving a target signal comprising speech in an essentially noise-free version s and in a noisy and/or processed version x, the monaural speech intelligibility predictor unit being configured to provide as an output a final monaural speech intelligibility predictor value d indicative of a listener's perception of said noisy and/or processed version x of the target signal, the monaural speech intelligibility predictor unit comprising a) A first input unit for providing a time-frequency representation s(k,m) of said noise-free version s of the target signal, k being a frequency bin index, k=1, 2, . . . , K, and m being a time index;

b) A second input unit for providing a time-frequency representation x(k,m) of said noisy and/or processed version x of the target signal, k being a frequency bin index, k=1, 2, . . . , K, and m being a time index;

c) A first envelope extraction unit for providing a time-frequency sub-band representation $s_j(n)$ of the noise-free version s of the target signal representing temporal envelopes, or functions thereof, of frequency sub-band signals $s_j(m)$ of said noise-free target signal, j being a frequency sub-band index, j=1, 2 . . . , J, and m being the time index;

d) A second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, . . . , J, and m being the time index;

e) A first time-frequency segment division unit for dividing said time-frequency sub-band representation $s_j(m)$ of the noise-free version s of the target signal into time-frequency segments $S_m$ corresponding to a number N of successive samples of said sub-band signals;

f) A second time-frequency segment division unit for dividing said time-frequency sub-band representation $x_j(m)$ of the noisy and/or processed version x of the target signal into time-frequency segments $X_m$ corresponding to a number N of successive samples of said sub-band signals;

g) An intermediate speech intelligibility calculation unit adapted for providing intermediate speech intelligibility coefficients $d_m$ estimating an intelligibility of said time-frequency segment $X_m$, said intermediate speech intelligibility coefficients $d_m$ being based on said essentially noise-free, optionally normalized and/or transformed, time frequency segments $\tilde{S}_m$, and said noisy and/or processed, optionally normalized and/or transformed, time-frequency segments $\tilde{X}_m$;

h) A final monaural speech intelligibility calculation unit for calculating a final monaural speech intelligibility predictor d estimating an intelligibility of said noisy and/or processed version x of the target signal by combining said intermediate speech intelligibility coefficients $d_m$, or a transformed version thereof, over time.

In an embodiment, the monaural speech intelligibility predictor unit comprises a normalization and transformation unit adapted for providing normalized and/or transformed versions $\tilde{X}_m$ ($\tilde{S}_m$) of said time-frequency segments $X_m$ ($S_m$).

In an embodiment, the normalization and transformation unit is configured to apply one or more algorithms for row and/or column normalization and/or transformation operations to the time-frequency segments $S_m$ and/or $X_m$. In an embodiment, the normalization and transformation unit is configured to provide at least one normalization and/or transformation operation of rows and at least one normalization and/or transformation operation of columns to the time-frequency segments $S_m$ and/or $X_m$.

In an embodiment, the monaural speech intelligibility predictor unit comprises a normalization and transformation unit configured to provide normalization and/or transformation of rows and columns of the time-frequency segments $S_m$ and $X_m$, wherein the normalization and/or transformation of rows comprise(s) at least one of the following operations R1) mean normalization of rows (cf. row normalization $g_1$ below), R2) unit-norm normalization of rows (cf. row normalization $g_2$ below), R3) Fourier transform of rows (cf. row transformation $g_3$ below), R4) providing a Fourier magnitude spectrum of rows (cf. row transformation $g_4$ below), and R5) providing the identity operation (cf. row transformation $g_5$ below), and wherein said normalization and/or transformation of columns comprises at least one of the following operations C1) mean normalization of columns (cf. column normalization $h_1$ below), and C2) unit-norm normalization of columns (cf. column normalization $h_2$ below).

In an embodiment, the final monaural speech intelligibility calculation unit is configured to combine said intermediate speech intelligibility coefficients $d_m$, or a transformed version thereof, by averaging over time, or by applying a MIN or MAX-function, or other algebraic or statistical function, to the intermediate speech intelligibility coefficients $d_m$, or a transformed version thereof.

In an embodiment, the first and second input units are configured to receive the noise free version of the target signal s (also termed the 'clean (version of the) target signal') and the noisy and/or processed version x of the target signal (termed the 'information signal x'), respectively, as a time variant (time domain/full band) signal s(n) and x(n), respectively, n being a time index. In an embodiment, the first and second input units are configured to receive the clean target signal s and the information signal x, respectively, in a time-frequency representation s(k,m) and x(k,m), respectively, from another unit or device, k and m being frequency and time indices, respectively. In an embodiment, the first and second input units each comprises a frequency decomposition unit for providing a time-frequency representation s(k,m) and x(k,m) of the clean target signal s and the information signal x from a time domain version of the respective signals (s(n) and x(n), n being a time index). In an embodiment, the frequency decomposition unit comprises a band-pass filterbank (e.g., a Gammatone filter bank), or is adapted to implement a Fourier transform algorithm (e.g. a short-time Fourier transform (STFT) algorithm).

In an embodiment, the monaural speech intelligibility predictor unit comprises a voice activity detector unit for indicating whether or not or to what extent a given time-segment of the essentially noise-free version s and the noisy and/or processed version x, respectively, of the target signal comprises or is estimated to comprise speech, and providing a voice activity control signal indicative thereof. In an embodiment, the voice activity detector unit is configured to provide a binary indication identifying segments comprising speech or no speech. In an embodiment, the voice activity detector unit is configured to identify segments comprising speech with a certain probability. In an embodiment, the voice activity detector is applied to a time-domain signal (or full-band signal, s(n), x(n), n being a time index). In an embodiment, the voice activity detector is applied to a time-frequency representation of a signal (s(k,m), x(k,m), or $s_j(m)$, $x_j(m)$, k and j being frequency indices (bin and sub-band, respectively), m being a time index) or a signal originating therefrom). In an embodiment, the voice activity detector unit is configured to identify time-frequency segments comprising speech on a time-frequency unit level (or e.g. in a frequency sub-band signal $x_j(m)$). In an embodiment, the monaural speech intelligibility predictor unit is adapted to receive (e.g. wirelessly receive) a voice activity control signal from another unit or device.

In an embodiment, the monaural speech intelligibility predictor unit comprises a voice activity detector unit for identifying time-segments of the essentially noise-free version s and the noisy and/or processed version x, respectively, of the target signal comprising or estimated to comprise speech, and wherein the monaural speech intelligibility predictor unit is configured to provide modified versions of the essentially noise-free version s and the noisy and/or processed version x, respectively, of the target signal comprising only such time segments comprising speech or being estimated to comprise speech.

In an embodiment, the first and second time-frequency segment division units are configured to base the generation of the time-frequency segments $S_m$ and $X_m$, respectively, or normalized and/or transformed versions, $\tilde{S}_m$ and $\tilde{X}_m$, thereof on the voice activity control signal, e.g. to generate said time-frequency segments in dependence of the voice activity control signal, e.g. only if speech is indicated to be present, or if the probability that the time-frequency segment in question contains speech is larger than a predefined value, e.g. 0.5).

In an embodiment, the monaural speech intelligibility predictor unit comprises a hearing loss model unit configured to apply a frequency dependent modification of the said noisy and/or processed version x of the target signal reflecting a deviation from normal hearing, e.g. a hearing impairment, of a relevant ear of the listener to provide a modified noisy and/or processed version x of the target signal for use together with said essentially noise-free version s of the target signal as a basis for calculating the final monaural speech intelligibility predictor d.

In an embodiment, the hearing loss model unit is configured to add a statistically independent noise signal, which is spectrally shaped according to an audiogram of the relevant ear of the listener, to said noisy and/or processed version x of the target signal.

The first and second envelope extraction units are configured for extracting a temporal envelope $s_j(m)$ and $x_j(m)$ comprising J sub-bands (j=1, 2, . . . , J) of the clean target signal s and the information signal x, respectively, from said time-frequency representation s(k,m) and x(k,m) of the clean target signal s and the information signal x, respectively. In an embodiment, the first and second envelope extraction units each comprises an algorithm for implementing a Hilbert transform, or for low-pass filtering the magnitude of complex-valued STFT signals s(k,m) and x(k,m), etc.

In an embodiment, the monaural speech intelligibility predictor unit is adapted to extract said temporal envelope signals $x_j(m)$ and $s_j(m)$, respectively, as $$z_j(m) = f\left(\sqrt{\sum_{k=k1(j)}^{k2(j)} |z(k,m)|^2}\right),$$

where z represent x or s, j=1, . . . , J and m=1, . . . , M, k1(j) and k2(j) denote DFT bin indices corresponding to lower and higher cut-off frequencies of the $j^{th}$ sub-band, J is the number of sub-bands, and M is the number of signal frames in the signal in question, and $f(\bullet)$ is a function.

In an embodiment, the function $f(\bullet)=f(w)$, where w represent $$\left(\sqrt{\sum_{k=k1(j)}^{k2(j)} |z(k,m)|^2}\right),$$

is selected among the following functions
 $f(w)=w$ representing the identity
 $f(w)=w^2$ providing power envelopes,
 $f(w)=2\cdot\log w$ or $f(w)=w^\beta$, $0<\beta<2$, allowing the modelling of the compressive non-linearity of the healthy cochlea,
or combinations thereof.

In an embodiment, the function $f(\bullet)=f(w)$, where w represents $$\left(\sqrt{\sum_{k=k1(j)}^{k2(j)} |z(k,m)|^2}\right),$$

is selected among the following functions
 $f(w)=w^2$ providing power envelopes,
 $f(w)=2\cdot\log w$ or $f(w)=w^\beta$, $0<\beta<2$, allowing the modelling of the compressive non-linearity of the healthy cochlea,
or combinations thereof.

In an embodiment, the first and second time-frequency segment division units are configured to divide said time-frequency representations $s_j(m)$ and $x_j(m)$, respectively, into segments in the form of spectrograms corresponding to N successive samples of all sub-band signals, wherein the $m^{th}$ segment $Z_m$ is defined by the J×N matrix $$Z_m = \begin{bmatrix} z_1(m-N+1) & \ldots & z_1(m) \\ \vdots & & \vdots \\ z_J(m-N+1) & \ldots & z_J(m) \end{bmatrix},$$

where z (Z) represents s (S) or x (X).

In an embodiment, the monaural speech intelligibility predictor unit comprises

A first optional normalization and/or transformation unit adapted for providing normalized and/or transformed versions $\tilde{S}_m$ of said time-frequency segments $S_m$;

A second optional normalization and/or transformation unit adapted for providing normalized and/or transformed versions $\tilde{X}_m$ of said time-frequency segments $X_m$;

In an embodiment, the normalization and/or transformation unit is configured to apply one or more algorithms for row and/or column normalization and/or transformation to the time-frequency segments $S_m$, and/or $X_m$, respectively.

In an embodiment, the normalization and/or transformation unit is configured to apply one or more of the following algorithms to the time-frequency segments $X_m$ and $S_m$, respectively, commonly denoted $Z_m$, where sub-script, time index m is skipped for simplicity in the following expressions:

R1) Normalization of rows to zero mean:

$$g_1(Z) = Z - \mu_z^r 1^T,$$

where $\mu_z^r$ is a J×1 vector whose j'th entry is the mean of the j'th row of Z, hence the superscript r in $\mu_z^r$, where 1 denotes an N×1 vector of ones, and where superscript T denotes matrix transposition;

R2) Normalization of rows to unit-norm:

$$g_2(Z) = D^r(Z)Z,$$

where $D^r(Z) = \text{diag}(\lfloor 1/\sqrt{Z(1,:)Z(:,)^H} \ldots 1/\sqrt{Z(J,:)Z(J,:)^H} \rfloor)$, where diag(•) is a diagonal matrix with the elements of the arguments on the main diagonal, and where Z(j,:) denotes the j'th row of Z, such that D'(Z) is a J×J diagonal matrix with the inverse norm of each row on the main diagonal, and zeros elsewhere, the superscript H denotes Hermitian transposition, and pre-multiplication with D'(Z) normalizes the rows of the resulting matrix to unit-norm;

R3) Fourier transformation applied to each row $$g_3(Z) = ZF,$$

where F is an N×N Fourier matrix;

R4) Fourier transformation applied to each row followed by computing the magnitude of the resulting complex-valued elements $$g_4 = |ZF|$$

where |•| computes the element-wise magnitudes;
R5) The identity operator $$g_5(Z) = Z.$$

C1) Normalization of columns to zero mean:

$$h_1(Z) = Z - 1\mu_z^{cT},$$

where $\mu_z^c$ is a N×1 vector whose $i^{th}$ entry is the mean of the $i^{th}$ row of Z, and where 1 denotes a J×1 vector of ones;

C2) Normalization of columns to unit-norm:

$$h_2(Z) = ZD^c(Z),$$

where $D^c(Z) = \text{diag}(\lfloor 1/\sqrt{Z(:,1)^H Z(:,1)} \ldots 1/\sqrt{Z(:,N)^H Z(:,N)} \rfloor)$, where Z(:, n) denotes the n'th row of Z, such that D'(Z) is a diagonal N×N matrix with the inverse norm of each column on the main diagonal, and zeros elsewhere, and where a post-multiplication with D'(Z) normalizes the rows of the resulting matrix to unit-norm.

In an embodiment, the intermediate speech intelligibility calculation unit is adapted to determine the intermediate speech intelligibility coefficients $d_m$ in dependence on a, e.g. linear, sample correlation coefficient d(a,b) of the elements in two K×1 vectors a and b, d(a,b) being defined by:

$$d(a,b) = \frac{\sum_{k=1}^{K}(a(k)-\mu_a)(b(k)-\mu_b)}{\sqrt{\sum_{k=1}^{K}(a(k)-\mu_a)^2(b(k)-\mu_b)^2}}, \text{ where}$$

$$\mu_a = \frac{1}{K}\sum_{k=1}^{K}a(k) \text{ and } \mu_b = \frac{1}{K}\sum_{k=1}^{K}b(k),$$

where k is the index of the vector entry and K is the vector dimension.

In an embodiment, a and b represent (e.g. any K) elements from time frequency segments $S_m$ (or $\tilde{S}_m$) and $X_m$ (or $\tilde{X}_m$), respectively.

In an embodiment, a and b represent elements from columns of time frequency segments $S_m$ (or $\tilde{S}_m$) and $X_m$ (or $\tilde{X}_m$), respectively. In an embodiment, a and b represent elements from rows of time frequency segments $S_m$ (or $\tilde{S}_m$) and $X_m$ (or $\tilde{X}_m$), respectively. In an embodiment, a and b represent all elements in time frequency segments $S_m$ (or $\tilde{S}_m$) and $X_m$ (or $\tilde{X}_m$), respectively.

In an embodiment, the intermediate intelligibility index $d_m$ is defined as 1) the average sample correlation coefficient of (some of) the (e.g. all) columns in $S_m$ and $X_m$, or $\tilde{S}_m$ and $\tilde{X}_m$, respectively, i.e., $$d_m = \frac{1}{N}\sum_{n=1}^{n}d(\tilde{S}_m(:,n), \tilde{X}_m(:,n)),$$

n being a column index, or as
2) the average sample correlation coefficient of (some of) the (e.g. all) rows in $S_m$ and $X_m$, or $\tilde{S}_m$ and $\tilde{X}_m$, i.e., $$d_m = \frac{1}{J}\sum_{j=1}^{J}d(\tilde{S}_m(j,:)^T, \tilde{X}_m(j,:)^T),$$

j being a row index, or as
3) the sample correlation coefficient of all elements in $S_m$ and $X_m$, or $\tilde{S}_m$ and $\tilde{X}_m$, i.e., $$d_m = d(\tilde{S}_m(:), \tilde{X}_m(:))$$

where the notation $S_m(:)$ and $X_m(:)$, or $\tilde{S}_m(:)$ and $\tilde{X}_m(:)$, represents NJ×1 vectors formed by stacking the columns of the respective matrices. In an embodiment, the number of columns N is 30 (or more). In an embodiment, the number of columns is 15 (or more). In an embodiment, N≤30 and J≤15).

In an embodiment, the final speech intelligibility calculation unit is adapted to calculate the final speech intelligibility predictor d from the intermediate speech intelligibility coefficients $d_m$, optionally transformed by a function $u(d_m)$, as an average over time of said noisy and/or processed version x of the target signal:

$$d = \frac{1}{M}\sum_{m=1}^{M} u(d_m)$$

where M represents the duration in time units of the speech active parts of said noisy and/or processed version x of the target signal. In an embodiment, the duration of the speech active parts of the noisy and/or processed version x of the target signal is defined as a (possibly accumulated) time period where the voice activity control signal indicates that the noisy and/or processed version x of the target signal comprises speech.

In an embodiment, the function $u(d_m)$ is defined as $$u(d_m) = \log\left(\frac{1}{1 - d_m^2}\right),$$

or as $$u(d_m) = d_m.$$

A Hearing Aid:

In an aspect, a hearing aid adapted for being located at or in left and right ears of a user, or for being fully or partially implanted in the head of the user, the hearing aid comprising a monaural speech intelligibility predictor unit as described above, in the detailed description of embodiments, in the drawings and in the claims is furthermore provided by the present disclosure.

In an embodiment, the hearing aid is configured to adaptively modify the processing of an input signal to the hearing aid to maximize the final monaural speech intelligibility predictor d. to enhance the user's intelligibility of an output signal of the hearing aid presented to the user In an embodiment, the hearing aid comprises
a) A number of input units $IU_i$, i=, ..., M, M being larger than or equal to one, each being configured to provide a time-variant electric input signal $y_i$ representing a sound input received at an $i^{th}$ input unit, the electric input signal $y_i$ comprising a target signal component and a noise signal component, the target signal component originating from a target signal source;
b) A configurable signal processor for processing the electric input signals and providing a processed signal u, which is connected to the hearing loss model of the monaural speech intelligibility predictor unit;
c) An output unit for creating output stimuli configured to be perceivable by the user as sound based on an electric output either in the form of the processed signal a from the signal processor or a signal derived therefrom; and
d) Antenna and transceiver unit for receiving a wireless signal s' comprising the target signal and for extracting an essentially noise-free version s of the target signal, which is connected to the monaural speech intelligibility predictor unit;
e) Wherein the final speech intelligibility predictor d is fed to the configurable signal processor.

The hearing aid (e.g. the monaural speech intelligibility predictor unit) preferably comprises a hearing loss model configured to provide that the input signal to the monaural speech intelligibility predictor unit (e.g. the output of the configurable processing unit, cf. e.g. FIG. 5B) is modified to reflect a deviation of a user's hearing profile from a normal hearing profile, e.g. to reflect a hearing impairment of the user.

In an embodiment, the configurable signal processor is adapted to control or influence the processing of the respective electric input signals, or one or more signals originating therefrom (e.g. a resulting beamformed signal) based on said final speech intelligibility predictor d provided by the monaural speech intelligibility predictor unit.

In an embodiment, the configurable signal processor is adapted to control or influence the processing of the respective electric input signals based on said final speech intelligibility predictor d when the target signal component comprises speech, such as only when the target signal component comprises speech (as e.g. defined by a voice (speech) activity detector).

In an embodiment, the configurable signal processor is adapted to control or influence the processing of the respective electric input signals to maximize the final speech intelligibility predictor d.

In an embodiment, the hearing aid is adapted to provide a frequency dependent gain and/or a level dependent compression and/or a transposition (with or without frequency compression) of one or frequency ranges to one or more other frequency ranges, e.g. to compensate for a hearing impairment of a user.

In an embodiment, the output unit comprises a number of electrodes of a cochlear implant or a vibrator of a bone conducting hearing aid. In an embodiment, the output unit comprises an output transducer. In an embodiment, the output transducer comprises a receiver (loudspeaker) for providing the stimulus as an acoustic signal to the user. In an embodiment, the output transducer comprises a vibrator for providing the stimulus as mechanical vibration of a skull bone to the user (e.g. in a bone-attached or bone-anchored hearing aid).

In an embodiment, the input unit comprises an input transducer for converting an input sound to an electric input signal. In an embodiment, the input unit comprises a wireless receiver for receiving a wireless signal comprising sound and for providing an electric input signal representing said sound. In an embodiment, the hearing aid comprises a directional microphone system adapted to enhance a target acoustic source among a multitude of acoustic sources in the local environment of the user wearing the hearing aid. In an embodiment, the directional system is adapted to detect (such as adaptively detect) from which direction a particular part of the microphone signal originates.

In an embodiment, the hearing aid comprises an antenna and transceiver circuitry for wirelessly receiving a direct electric input signal from another device, e.g. a communication device or another hearing aid. In general, a wireless link established by antenna and transceiver circuitry of the hearing aid can be of any type. In an embodiment, the wireless link is used under power constraints, e.g. in that the hearing aid comprises a portable (typically battery driven) device.

In an embodiment, the hearing aid comprises a forward or signal path between an input transducer (microphone system and/or direct electric input (e.g. a wireless receiver)) and an output transducer. In an embodiment, the signal processor is located in the forward path. In an embodiment, the signal processor is adapted to provide a frequency dependent gain according to a user's particular needs. In an embodiment, the hearing aid comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing aid comprises an analogue-to-digital (AD) converter to digitize an analogue input with a predefined sampling rate, e.g. 20 kHz. In an embodiment, the hearing aid comprises a digital-to-analogue (DA) converter to convert a digital signal to an analogue output signal, e.g. for being presented to a user via an output transducer.

In an embodiment, the hearing aid comprises a number of detectors configured to provide status signals relating to a current physical environment of the hearing aid (e.g. the current acoustic environment), and/or to a current state of the user wearing the hearing aid, and/or to a current state or mode of operation of the hearing aid. Alternatively or additionally, one or more detectors may form part of an external device in communication (e.g. wirelessly) with the hearing aid. An external device may e.g. comprise another hearing aid, a remote control, and audio delivery device, a telephone (e.g. a Smartphone), an external sensor, etc. In an embodiment, one or more of the number of detectors operate(s) on the full band signal (time domain). In an embodiment, one or more of the number of detectors operate(s) on band split signals ((time-) frequency domain).

In an embodiment, the hearing aid further comprises other relevant functionality for the application in question, e.g. compression, noise reduction, feedback reduction, etc.

Use of a Monaural Speech Intelligibility Predictor Unit:

In an aspect, use of a monaural speech intelligibility predictor unit as described above, in the detailed description of embodiments, in the drawings and in the claims in a hearing aid to modify signal processing in the hearing aid aiming at enhancing intelligibility of a speech signal presented to a user by the hearing aid is furthermore provided by the present disclosure. In an embodiment, use of a monaural speech intelligibility predictor unit in a hearing aid in a noisy environment is provided (e.g. a car telephony situation, or other listening situation where a (e.g. substantially clean version of the) target speech signal is received wirelessly and acoustic noise is present at the user's ears) to enhance a user's intelligibility of speech in a noisy environment. In an embodiment, use of a monaural speech intelligibility predictor unit in an active ear protection device is provided.

A Method of Providing a Monaural Speech Intelligibility Predictor:

In a further aspect, a method of providing a monaural speech intelligibility predictor for estimating a user's ability to understand an information signal x comprising a noisy and/or processed version of a target speech signal is provided. The method comprises providing a time-frequency representation s(k,m) of said noise-free version s of the target signal, k being a frequency bin index, k=1, 2, . . . , K, and m being a time index;

providing a time-frequency representation x(k,m) of said noisy and/or processed version x of the target signal, k being a frequency bin index, k=1, 2, . . . , K, and m being a time index;

providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, . . . , J, and m being the time index;

providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=, 2, . . . , J, and m being the time index;

dividing said time-frequency sub-band representation $s_j(m)$ of the noise-free version s of the target signal into time-frequency segments $S_m$ corresponding to a number N of successive samples of said sub-band signals;

dividing said time-frequency sub-band representation $x_j(m)$ of the noisy and/or processed version x of the target signal into time-frequency segments $X_m$ corresponding to a number N of successive samples of said sub-band signals;

providing intermediate speech intelligibility coefficients $d_m$ estimating an intelligibility of said time-frequency segment $X_m$, said intermediate speech intelligibility coefficients $d_m$ being based on said essentially noise-free, normalized and/or transformed time frequency segments $\tilde{S}_m$, and said noisy and/or processed, normalized and/or transformed time-frequency segments $\tilde{X}_m$;

calculating a final monaural speech intelligibility predictor d estimating an intelligibility of said noisy and/or processed version x of the target signal by combining, e.g. by averaging or applying a MIN or MAX-function, said intermediate speech intelligibility coefficients $d_m$, or a transformed version thereof, over time.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

In an embodiment, the method comprises subjecting a speech signal (a signal comprising speech) to a hearing loss model configured to model imperfections of an impaired auditory system to thereby provide said information signal x. By subjecting the speech signal (e.g. signal x' in FIG. 3A) to a hearing loss model (HLM in FIG. 3A), the resulting information signal x can be used as an input to the speech intelligibility predictor (MSIP in FIG. 3A), thereby providing a measure of the intelligibility of the speech signal for an unaided hearing impaired person. In an embodiment, the hearing loss model is a generalized model reflecting a hearing impairment of an average hearing impaired user. In an embodiment, the hearing loss model is configurable to reflect a hearing impairment of a particular user. e.g. including a frequency dependent hearing loss (deviation of a hearing threshold from a(n average) hearing threshold of a normally hearing person). By subjecting a speech signal (e.g. signal y in FIG. 3C) to a signal processing (e.g. SPU in FIG. 3C) intended to compensate for the user's hearing impairment, AND to a hearing loss model (HLM in FIG. 3C) the resulting information signal x can be used as an input to the speech intelligibility predictor (cf. e.g. MSIP in FIG.

3C), thereby providing a measure d of the intelligibility of the speech signal for an aided hearing impaired person. Such scheme may e.g. be used to evaluate the influence of different processing algorithms (and/or modifications of processing algorithms) on the user's (estimated) intelligibility of the resulting information signal (cf. e.g. FIG. 3B) or be used to online optimization of signal processing in a hearing aid (cf. e.g. 3C).

In an embodiment, the method comprises adding noise to a target speech signal to provide said information signal x, which is used as input to the method of providing a monaural speech intelligibility predictor value. The addition of a predetermined (or varying) amount of noise to an information signal can be used to—in a simple way—emulate a hearing loss of a user (to provide the effect of a hearing loss model). In an embodiment, the target signal is modified (e.g. attenuated) according to the hearing loss of a user, e.g. an audiogram. In an embodiment, noise is added to a target signal AND the target signal is attenuated to reflect a hearing loss of a user.

A Binaural Hearing (Aid) System:

In an aspect, a (first) binaural hearing system comprising left and right hearing aids as described above, in the detailed description of embodiments and drawings and in the claims is furthermore provided.

In an embodiment, each of the left and right hearing aids comprises antenna and transceiver circuitry for allowing a communication link to be established and information to be exchanged between said left and right hearing aids.

In an embodiment, the binaural hearing system further comprises a binaural speech intelligibility prediction unit for providing a final binaural speech intelligibility measure $d_{binaural}$ of the predicted speech intelligibility of the user, when exposed to said sound input, based on the monaural speech intelligibility predictor values $d_{left}$, $d_{right}$ of the respective left and right hearing aids.

In an embodiment, the final binaural speech intelligibility measure $d_{binaural}$ is determined as the maximum of the speech intelligibility predictor values $d_{left}$, $d_{right}$ of the respective left and right hearing aids: $d_{binaural}=\max(d_{left}, d_{right})$. Thereby a relatively simple system is provided implementing a better ear approach. In an embodiment, the binaural hearing system is adapted to activate such approach when an asymmetric listening situation is detected or selected by the user, e.g. a situation where a speaker is located predominantly to one side of the user wearing the binaural hearing system, e.g. when sitting in a car.

In an embodiment, the respective configurable signal processors of the left and right hearing aids are adapted to control or influence the processing of the respective electric input signals based on said final binaural speech intelligibility measure $d_{binaural}$. In an embodiment, the respective configurable signal processors of the left and right hearing aids are adapted to control or influence the processing of the respective electric input signals to maximize said final binaural speech intelligibility measure $d_{binaural}$.

In an embodiment, the binaural hearing system further comprises an auxiliary device.

In an embodiment, the system is adapted to establish a communication link between the hearing aid(s) and the auxiliary device to provide that information (e.g. control and status signals, possibly audio signals) can be exchanged or forwarded from one to the other.

In an embodiment, the auxiliary device is or comprises a remote control for controlling functionality and operation of the hearing aid(s). In an embodiment, the function of a remote control is implemented in a SmartPhone, the SmartPhone possibly running an APP allowing to control the functionality of the audio processing device via the SmartPhone (the hearing aid(s) comprising an appropriate wireless interface to the SmartPhone, e.g. based on Bluetooth or some other standardized or proprietary scheme).

An APP:

In a further aspect, a non-transitory application, termed an APP, is furthermore provided by the present disclosure. The APP comprises executable instructions configured to be executed on an auxiliary device to implement a user interface for a hearing aid or a hearing system described above in the 'detailed description of embodiments', and in the claims. In an embodiment, the APP is configured to run on cellular phone, e.g. a smartphone, or on another portable device allowing communication with said hearing aid or said hearing system.

A Computer Readable Medium:

In an aspect, a tangible computer-readable medium storing a computer program comprising program code means for causing a data processing system to perform at least some (such as a majority or all) of the steps of any one of the methods described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the any one of the methods described above, in the 'detailed description of embodiments' and in the claims is furthermore provided by the present application.

A Computer Program:

A computer program (product) comprising instructions which, when the program is executed by a computer, cause the computer to carry out (steps of) the method described above, in the 'detailed description of embodiments' and in the claims is furthermore provided by the present application.

Definitions

In the present context, a 'hearing aid' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing aid' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing aid may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing aid may comprise a single unit or several units communicating electronically with each other.

More generally, a hearing aid comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit for processing the input audio signal and an output means for providing an audible signal to the user in dependence on the processed audio signal. In some hearing aids, an amplifier may constitute the signal processing circuit. The signal processing circuit typically comprises one or more (integrated or separate) memory elements for executing programs and/or for storing parameters used (or potentially used) in the processing and/or for storing information relevant for the function of the hearing aid and/or for storing information (e.g. processed information, e.g. provided by the signal processing circuit). e.g. for use in connection with an interface to a user and/or an interface to a programming device. In some hearing aids, the output means may comprise an output transducer, such as e.g. a loudspeaker for providing an air-borne acoustic signal or a vibrator for providing a structure-borne or liquid-borne acoustic signal. In some hearing aids, the output means may comprise one or more output electrodes for providing electric signals.

In some hearing aids, the vibrator may be adapted to provide a structure-borne acoustic signal transcutaneously or percutaneously to the skull bone. In some hearing aids, the vibrator may be implanted in the middle ear and/or in the inner ear. In some hearing aids, the vibrator may be adapted to provide a structure-borne acoustic signal to a middle-ear bone and/or to the cochlea. In some hearing aids, the vibrator may be adapted to provide a liquid-borne acoustic signal to the cochlear liquid, e.g. through the oval window. In some hearing aids, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing system' refers to a system comprising one or two hearing aids, and a 'binaural hearing system' refers to a system comprising two hearing aids and being adapted to cooperatively provide audible signals to both of the user's ears. Hearing systems or binaural hearing systems may further comprise one or more 'auxiliary devices', which communicate with the hearing aid(s) and affect and/or benefit from the function of the hearing aid(s). Auxiliary devices may be e.g. remote controls, audio gateway devices, mobile phones (e.g. SmartPhones), public-address systems, car audio systems or music players. Hearing aids, hearing systems or binaural hearing systems may e.g. be used for compensating for a hearing-impaired person's loss of hearing capability, augmenting or protecting a normal-hearing person's hearing capability and/or conveying electronic audio signals to a person.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Figure 1A:
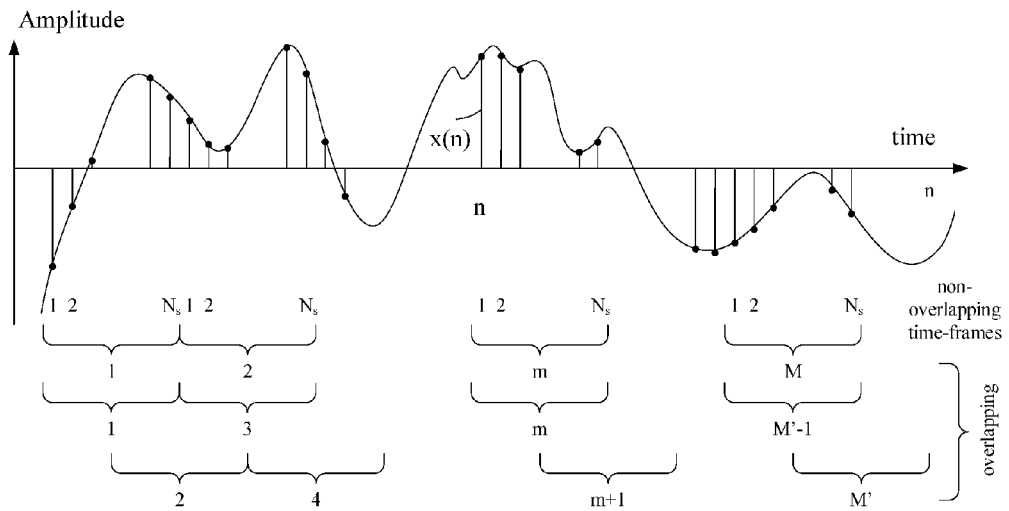
FIG. 1A schematically shows a time variant analogue signal (Amplitude vs time) and its digitization in samples, the samples being arranged in a number of time frames, each comprising a number $N_s$ of samples.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing aids or hearing aid systems.

The present disclosure relates to signal processing methods for predicting the intelligibility of speech, e.g., the output signal of a signal processing device such as a hearing aid. The intelligibility prediction is made in the form of an index that correlates highly with the fraction of words that an average listener would be able to understand from some speech material. For situations where an estimate of absolute intelligibility, i.e., the actual percentage of words understood, is desired, this index may be transformed to a number in the range 0-100 percent, see e.g. [3] for one method to do this.

The method proposed here belongs to the class of so-called intrusive methods. Methods in this class are characterized by the fact that they make their intelligibility prediction by comparing the noisy—and potentially signal processed—speech signal, with a noise-free, undistorted version of the underlying speech signal, see [1, 2, 3] for examples of existing methods. The assumption that a noise-free reference signal is available is reasonable in many practically relevant situations. For example, when evaluating the impact of various hearing aid signal processing algorithms on intelligibility, one normally conducts a listening test with human subjects. In preparing such a test, the stimuli are often created artificially by explicitly adding noise signal to noise-free speech signals—in other words, noise-free signals are readily available. Hence, the proposed intelligibility prediction algorithm allows one to replace a costly and time-consuming listening test involving human subjects, with machine predictions.

Much of the signal processing of the present disclosure is performed in the time-frequency domain, where a time domain signal is transformed into the (time-)frequency domain by a suitable mathematical algorithm (e.g. a Fourier transform algorithm) or filter (e.g. a filter bank).

FIG. 1A schematically shows a time variant analogue signal (Amplitude vs time) and its digitization in samples, the samples being arranged in a number of time frames, each comprising a number $N_s$ of digital samples. FIG. 1A shows an analogue electric signal (solid graph), e.g. representing an acoustic input signal, e.g. from a microphone, which is converted to a digital audio signal in an analogue-to-digital (AD) conversion process, where the analogue signal is sampled with a predefined sampling frequency or rate $f_s$, $f_s$ being e.g. in the range from 8 kHz to 40 kHz (adapted to the particular needs of the application) to provide digital samples x(n) at discrete points in time n, as indicated by the vertical lines extending from the time axis with solid dots at its endpoint coinciding with the graph, and representing its digital sample value at the corresponding distinct point in time n. Each (audio) sample x(n) represents the value of the acoustic signal at n by a predefined number $N_b$ of bits, $N_b$ being e.g. in the range from 1 to 16 bits. A digital sample x(n) has a length in time of $1/f_s$, e.g. 50 µs, for $f_s$=20 kHz. A number of (audio) samples $N_s$ are arranged in a time frame, as schematically illustrated in the lower part of FIG. 1A, where the individual (here uniformly spaced) samples are grouped in time frames (1, 2, . . . , $N_s$)). As also illustrated in the lower part of FIG. 1A, the time frames may be arranged consecutively to be non-overlapping (time frames 1, 2, . . . , m, . . . , M) or overlapping (here 50%, time frames 1, 2, . . . , m, . . . , M'), where in is time frame index. In an embodiment, a time frame comprises 64 audio data samples. Other frame lengths may be used depending on the practical application.

Figure 1B:
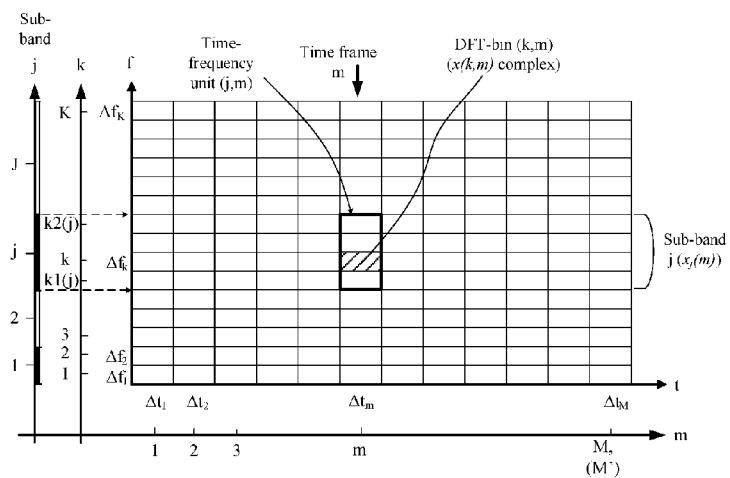
FIG. 1B illustrates a time-frequency map representation of the time variant electric signal of FIG. 1A, FIG. 2A symbolically shows an intrusive monaural speech intelligibility predictor unit providing a monaural speech intelligibility predictor d based on a time-frequency representation $x_j(m)$ of an information signal x.

FIG. 1B schematically illustrates a time-frequency representation of the (digitized) time variant electric signal x(n) of FIG. 1A. The time-frequency representation comprises an array or map of corresponding complex or real values of the signal in a particular time and frequency range. The time-frequency representation may e.g. be a result of a Fourier transformation converting the time variant input signal x(n) to a (time variant) signal x(k,m) in the time-frequency domain. In an embodiment, the Fourier transformation comprises a discrete Fourier transform algorithm (DFT). The frequency range considered by a typical hearing device (e.g. a hearing aid) from a minimum frequency $f_{min}$ to a maximum frequency $f_{max}$ comprises a part of the typical human audible frequency range from 20 Hz to 20 kHz, e.g. a part of the range from 20 Hz to 12 kHz. In FIG. 1B, the time-frequency representation x(k,m) of signal x(n) comprises complex values of magnitude and/or phase of the signal in a number of DFT-bins defined by indices (k,m), where k=1, . . . , K represents a number K of frequency values (cf. vertical k-axis in FIG. 1B) and m=1, . . . , M (M') represents a number M (M') of time frames (cf. horizontal m-axis in FIG. 1B). A time frame is defined by a specific time index m and the corresponding K DFT-bins (cf. indication of Time frame m in FIG. 1B). A time frame m represents a frequency spectrum of signal x at time m. A DFT-bin (k,m) comprising a (real) or complex value x(k,m) of the signal in question is illustrated in FIG. 1B by hatching of the corresponding field in the time-frequency map. Each value of the frequency index k corresponds to a frequency range $\Delta f_k$, as indicated in FIG. 1B by the vertical frequency axis $f$. Each value of the time index m represents a time frame. The time $\Delta t_m$ spanned by consecutive time indices depend on the length of a time frame (e.g. 25 ms) and the degree of overlap between neighbouring time frames (cf. horizontal t-axis in FIG. 1B).

In the present application, a number J of (non-uniform) frequency sub-bands with sub-band indices j=1, 2, . . . , J is defined, each sub-band comprising one or more DFT-bins (cf. vertical Sub-band j-axis in FIG. 1B). The $j^{th}$ sub-band (indicated by Sub-band j ($x_j(m)$) in the right part of FIG. 1B) comprises DFT-bins with lower and upper indices k1(j) and k2(j), respectively, defining lower and upper cut-off frequencies of the $j^{th}$ sub-band, respectively. A specific time-frequency unit (j,m) is defined by a specific time index m and the DFT-bin indices k1(j)-k2(j), as indicated in FIG. 1B by the bold framing around the corresponding DFT-bins. A specific time-frequency unit (j,m) contains complex or real values of the $j^{th}$ sub-band signal $x_j(m)$ at time m.

Figure 2A:
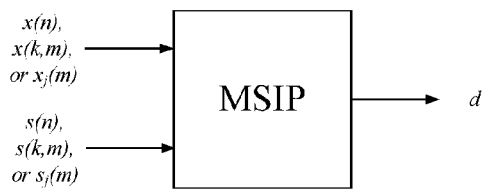
FIG. 2B shows a first embodiment an intrusive monaural speech intelligibility predictor unit.
FIG. 2C shows a second embodiment an intrusive monaural speech intelligibility predictor unit.

FIG. 2A symbolically shows an intrusive monaural speech intelligibility predictor unit (MSIP) providing a monaural speech intelligibility predictor d based on either
time domain versions s(n), x(n) (n being a time (sample) index),
time-frequency band representations s(k,m), x(k,m) (k being a frequency index, m being a time (frame) index), or
sub-band representations $s_j(m)$, $x_j(m)$ (j being a frequency sub-band index) of an essentially noise-free (clean) version of a target signal s and a noisy and/or processed version x of the target signal s comprising speech, respectively.

Figure 2B:
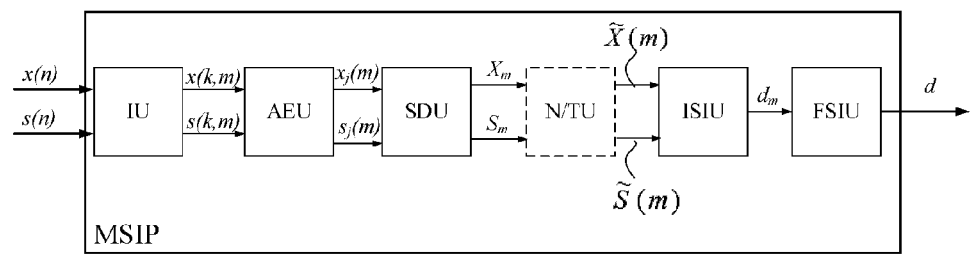

FIG. 2B shows a first embodiment an intrusive monaural speech intelligibility predictor unit (MSIP). The intrusive monaural speech intelligibility predictor unit (MSIP) is adapted for receiving a target signal comprising speech in an essentially noise-free version s(n) and in a noisy and/or processed version x(n), where n is a time index. The monaural speech intelligibility predictor unit is configured to provide as an output a final monaural speech intelligibility predictor value d indicative of a listener's (user's) perception of the noisy and/or processed version x of the target signal.

The monaural speech intelligibility predictor unit (MSIP) comprises a first input unit (IU) for providing a time-frequency representation s(k,m) of said noise-free version s of the target signal from the time variant signal s(n), and a second input unit (IU) for providing a time-frequency representation x(k,m) of the noisy and/or processed version x of the target signal from the time variant signal x(n), k being a frequency bin index, k=1, 2, . . . , K, and m being a time index.

The monaural speech intelligibility predictor unit (MSIP) further comprises a first envelope extraction unit (AEU) for providing a time-frequency sub-band representation $s_j(m)$ of the noise-free version s of the target signal representing temporal envelopes, or functions thereof, of frequency sub-band signals $s_j(m)$ of said noise-free target signal from the time-frequency representation s(k,m), and a second envelope extraction unit (AEU) for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal from the time-frequency representation s(k,m), j=1, 2, . . . , J, and m being the time index.

The monaural speech intelligibility predictor unit (MSIP) further comprises a first time-frequency segment division unit (SDU) for dividing said time-frequency sub-band representation $s_j(m)$ of the noise-free version s of the target signal into time-frequency segments $S_m$ corresponding to a number N of successive samples of the sub-band signals $s_j(m)$, and a second time-frequency segment division unit (SDU) for dividing the time-frequency sub-band representation $x_j(n)$ of the noisy and/or processed version x of the target signal into time-frequency segments $X_m$ corresponding to a number N of successive samples of the sub-band signals $x_j(m)$.

The monaural speech intelligibility predictor unit (MSIP) further optionally comprises a first normalization and/or transformation unit (N/TU) adapted for providing normalized and/or transformed versions $\tilde{S}_m$ of the time-frequency segments $S_m$, and optionally a second normalization and/or transformation unit (N/TU) adapted for providing normalized and/or transformed versions $\tilde{X}_m$ of the time-frequency segments $X_m$.

The monaural speech intelligibility predictor unit (MSIP) further comprises an intermediate speech intelligibility calculation unit (ISIU) adapted for providing intermediate speech intelligibility coefficients $d_m$ estimating an intelligibility of the time-frequency segment $X_m$, wherein the intermediate speech intelligibility coefficients $d_m$ are based on the essentially noise-free, optionally normalized and/or transformed, time frequency segments $S_m$, $\tilde{S}_m$, and the noisy and/or processed, optionally normalized and/or transformed, time-frequency segments $X_m$, $\tilde{X}_m$.

The monaural speech intelligibility predictor unit (MSIP) further comprises a final monaural speech intelligibility calculation unit (FSIU) for calculating a final monaural speech intelligibility predictor d estimating an intelligibility of the noisy and/or processed version x of the target signal by combining, e.g. by averaging or applying a MIN or MAX-function, the intermediate speech intelligibility coefficients $d_m$, or a transformed version thereof, over time.

Figure 2C:
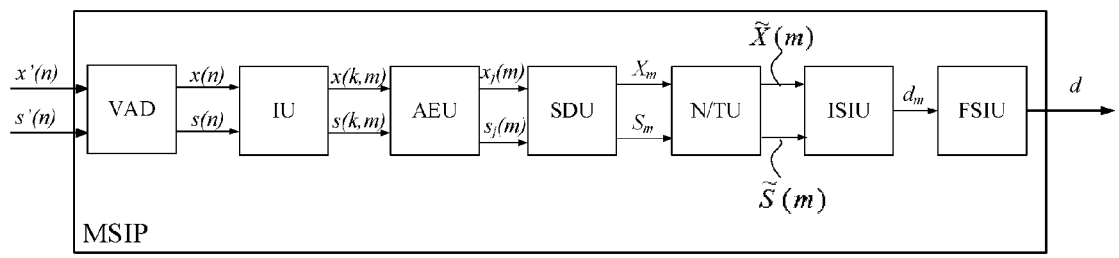

FIG. 2C shows a second embodiment an intrusive monaural speech intelligibility predictor unit (MSIP). The embodiment of FIG. 2C comprises the same functional units as described in connection with FIG. 2B. Additionally, it comprises a voice activity detector unit (VAD) for indicating whether or not or to what extent a given time-segment of the essentially noise-free version s (s'(n) in FIG. 2C) and the noisy and/or processed version x (x'(n) in FIG. 2C), respectively, of the target signal comprises or is estimated to comprise speech, and providing a voice activity control signal indicative thereof. In the embodiment of FIG. 2C, the voice activity detector unit (VAD) itself is configured to provide modified versions of the essentially noise-free version s and the noisy and/or processed version x, respectively, of the target signal comprising only time segments comprising speech or being estimated to comprise speech (in FIG. 2C denoted s(n) and x(n) respectively). Alternatively, the modified signals s(n) and x(n) may be created in respective separation units.

Figure 3A:
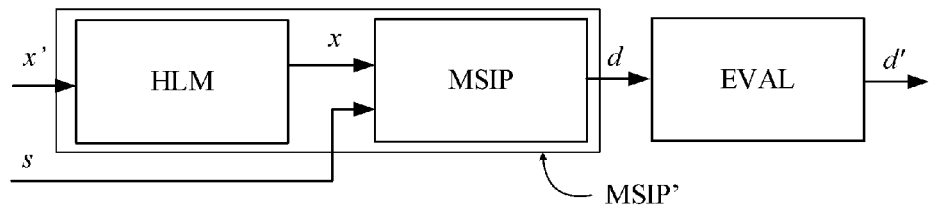
FIG. 3A shows an intrusive monaural speech intelligibility predictor unit in combination with a hearing loss model and an evaluation unit.
Figure 3B:
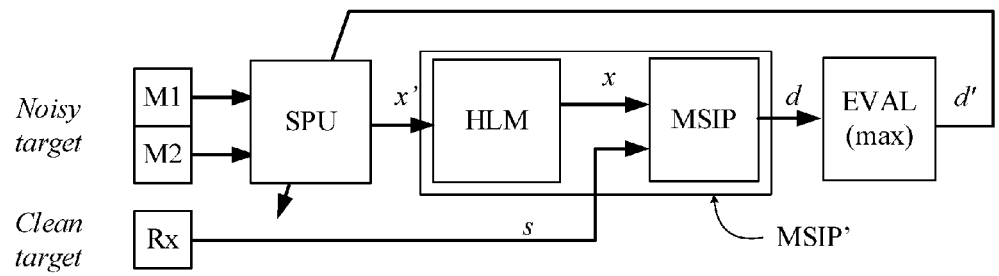
FIG. 3B shows an intrusive monaural speech intelligibility predictor unit in combination with a signal processor and an evaluation unit.
Figure 3C:
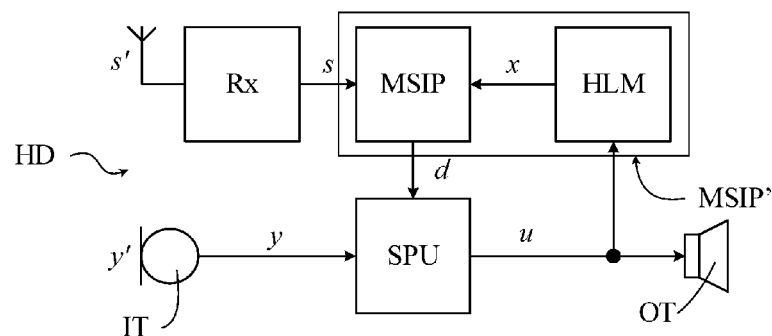
FIG. 3C shows a first embodiment of a hearing aid comprising an intrusive monaural speech intelligibility predictor unit with a hearing loss model configured to optimize a user's intelligibility of an output signal of the hearing aid.

In order to simulate the potential decrease in intelligibility due to a hearing loss, an optional hearing loss model is included (cf. FIG. 3A, 3B, 3C). Several methods for simulating a hearing loss exist [4]. Typically, a hearing loss model builds (at least) on an audiogram containing frequency dependent hearing thresholds of a user (or representative of a type of hearing loss). The, perhaps, simplest hearing loss model consists of adding to the input signal x(n) a statistically independent noise signal, which is spectrally shaped according to the audiogram of the listener [5].

The proposed monaural, intrusive speech intelligibility predictor may be decomposed into a number of sub-stages as illustrated in FIGS. 2B and 2C and discussed above. Each sub-stage is described in more detail in the following.

Voice Activity Detection (VAD).

Speech intelligibility (SI) relates to regions of the input signal with speech activity—silence regions do no contribute to SI. Hence, the first step is to detect voice activity regions in the input signals. Since the noise-free speech signal s'(n) is available, voice activity is trivial. For example, in [3] the noise-free speech signal s'(n) was divided into successive frames. Speech-active frames were then identified as the ones with a frame-energy no less than e.g. 40 dB of the frame with maximum energy. The speech inactive frames, i.e., the ones with energy less than e.g., 40 dB of the maximum frame energy, are then discarded from both signals, x'(n) and s'(n). Let us denote the input signals with speech activity by x(n) and s(n), respectively, where n is a discrete-time index. A voice activity detector is shown in FIG. 2C as unit VAD.

Frequency Decomposition (IU) and Envelope Extraction (AEU)

The first step is to perform a frequency decomposition (cf. input unit IU in FIG. 2C) of the signals x(n) and s(n). This may be achieved in many ways, e.g., using a short-time Fourier transform (STFT), a band-pass filterbank (e.g., a Gamma-tone filter bank), etc. Subsequently, the temporal envelopes of each sub-band signal are extracted (cf. unit AEU in FIG. 2C). This may, e.g., be achieved using a Hilbert transform, or by low-pass filtering the magnitude of complex-valued STFT signals, etc.

As an example, we describe in the following how the frequency decomposition and envelope extraction can be achieved using an STFT; the described procedure is similar to the one in [3]. Let us assume, as an example, that signals are sampled with a frequency of $f_s=10000$ Hz. First, a time-frequency representation is obtained by segmenting signals x(n) and s(n) into (e.g. 50%) overlapping, windowed frames (cf. e.g. FIG. 1A). Normally, a tapered window, e.g. a Hanning-window, is used. The window length may e.g. be 256 samples when the sample rate is 10000 Hz. Then, each frame is Fourier transformed using a fast Fourier transform (FFT) (potentially after appropriate zero-padding). The resulting DFT bins may be grouped in perceptually relevant sub-bands. For example, one could use one-third octave bands (e.g. as in [4]), but it should be clear that any other sub-band division can be used (for example, the grouping could be uniform, i.e., unrelated to perception in this respect, cf. FIG. 1B). In the case of one-third octave bands and a sampling rate of 10000 Hz, there are 15 bands which cover the frequency range 150-5000 Hz. Other numbers of bands and another frequency range can be used. We refer to the time-frequency tiles defined by these frames and sub-bands as time-frequency (TF) units (or STFT coefficients), cf. FIG. 1B. Applying this to the noisy/processed input signal x(n) leads to (generally complex-valued) STFT coefficients x(k, m), where k and m denote frequency and frame (time) indices, respectively. STFT coefficients s(k,m) for the noise-free reference speech signal are found in a similar manner.

Temporal envelope signals may then be extracted as $$x_j(m) = f\left(\sqrt{\sum_{k=k1(j)}^{k2(j)} |x(k,m)|^2}\right), j = 1, \ldots J, \text{ and}$$

$$m = 1, \ldots M,$$

where k1(j) and k2(j) denote DFT bin indices corresponding to lower and higher cut-off frequencies of the $j^{th}$ sub-band, J is the number of sub-bands (e.g. 16), and M is the number of signal frames in the signal in question, and where the function $f(x)$ is included for generality. For example, for $f(x)=x$, we get the temporal envelope used in [4], with $f(x)=x^2$, we extract power envelopes, and with $f(x)=2 \log x$, or $f(x)=x^\beta$, $0<\beta<2$, we can model the compressive non-linearity of the healthy cochlea, respectively. It should be clear that other reasonable choices for $f(x)$ exist. Temporal envelope signals $s_j(m)$ for the noise-free speech signal are found in a similar manner. The same choice of $f(x)$ may be used in both cases.

As mentioned, other envelope representations may be implemented, e.g., using a Gammatone filterbank, followed by a Hilbert envelope extractor, etc., and functions $f(x)$ may be applied to these envelopes in a similar manner as described above for STFT based envelopes. In any case, the result of this procedure is a time-frequency representation in terms of sub-band temporal envelopes, $x_j(m)$ and $s_j(m)$, where j is a sub-band index, and m is a time index.

Time-Frequency Segments (SDU)

Next, we divide the time-frequency representations $x_j(m)$ and $s_j(m)$ into segments, i.e., spectrograms corresponding to N successive samples of all sub-band signals. For example, the $m^{th}$ segment for the noisy/processed signal is defined by the J×N matrix $$X_m = \begin{bmatrix} x_1(m-N+1) & \cdots & x_1(m) \\ \vdots & & \vdots \\ x_J(m-N+1) & \cdots & x_J(m) \end{bmatrix}.$$

The corresponding segment $S_m$ for the noise-free reference signal is found in an identical manner.

It should be understood that other versions of the time-segments could be used, e.g., segments, which have been shifted in time to operate on frame indices m−N/2+1 through m+N/2.

Normalizations and Transformation of Time-Frequency Segments (N/TU)

The rows and columns of each segment $X_m$ and $S_m$ may be normalized/transformed in various ways (below, we show the normalizations/transformations as applied to $X_m$; they are applied to $S_m$ in a completely analogously manner. The same normalization/transformation is applied to both $X_m$ and $S_m$). In particular, we consider the following row (R) normalizations/transformations R1) Normalization of rows to zero mean:

$$g_1(X) = X - \mu_x^r 1^T,$$

where $\mu_x^r$ is a J×1 vector whose $j^{th}$ entry is the mean of the $j^{th}$ row of X (hence the superscript r in $\mu_x^r$), and where 1 denotes an N×1 vector of ones.

R2) Normalization of rows to unit-norm:

$$g_2(X) = D^r(X)X,$$

where $$D^r(X) = \text{diag}([1/\sqrt{X(1,:)X(1,:)^H} \ldots 1/\sqrt{X(J,:)X(J,:)^H}]),$$

and where diag(•) is a diagonal matrix with the elements of the arguments on the main diagonal. Furthermore, X(j,:) denotes the $j^{th}$ row of X, such that $D^r(X)$ is a J×J diagonal matrix with the inverse norm of each row on the main diagonal, and zeroes elsewhere (the superscript H denotes Hermitian transposition). Pre-multiplication with $D^r(X)$ normalizes the rows of the resulting matrix to unit-norm.

R3) Fourier transformation applied to each row $$g_3(X) = XF,$$

where F is an N×N Fourier matrix.

R4) Fourier transformation applied to each row followed by computing the magnitude of the resulting complex-valued elements $$g_4(X) = |XF|,$$

where |•| computes the element-wise magnitudes.

R5) The identity operator $$g_5(X) = X.$$

We consider the following column (C) normalizations

C1) Normalization of columns to zero mean:

$$h_1(X) = X - 1\mu_x^{cT},$$

where $\mu_x^c$ is a N×1 vector whose $i^{th}$ entry is the mean of the $i^{th}$ row of X, and where 1 denotes an J×1 vector of ones.

C2) Normalization of columns to unit-norm:

$$h_2(X) = XD^c(X), \text{ where}$$

$$D^c(X) = \text{diag}([1/\sqrt{X(:,1)^H X(:,1)} \ldots 1/\sqrt{X(:,N)^H X(:,N)}]).$$

Here X(:,n) denotes the $n^{th}$ row of X, such that $D^r(X)$ is a diagonal N×N matrix with the inverse norm of each column on the main diagonal, and zeros elsewhere. Post-multiplication with $D^c(X)$ normalizes the rows of the resulting matrix to unit-norm.

The row—(R#, #=1, 2, . . . , 5) and column (C#, #=1, 2) normalizations/transformations listed above may be combined in different ways. In a preferred embodiment, at least one of row normalizations/transformations $g_i(•)$ (i=1, 2, . . . , 5) and at least one of the column normalizations/transformations $h_j(•)$ (j=1, 2) is applied (in any order).

One combination of particular interest is where, first, the rows are normalized to zero-mean and unit-norm, followed by a similar mean and norm normalization of the columns. This particular combination may be written as $$\tilde{X}_m = h_2(h_1(g_2(g_1(X_m)))),$$

where $\tilde{X}_m$ is the resulting row- and column normalized matrix.

Another transformation of interest is to compute the magnitude Fourier spectrum of each row of matrix $X_m$ followed by mean- and norm-normalization of the resulting columns. With the introduced notation, this may be written simply as $$\tilde{X}_m = h_2(h_1(g_3(X_m))).$$

Other combinations of these normalizations/transformations may be of interest, e.g., $$\tilde{X}_m = g_2(g_1(h_2(h_1(X_m))))$$

(mean- and norm-standardization of the columns followed by mean- and norm-standardization of the rows), etc. As mentioned, a particular combination of row- and column-normalizations/transformations is chosen and applied to all segments $X_m$ and $S_m$ of the noisy/processed and noise-free signal, respectively.

Estimation of Intermediate Intelligibility Coefficients (ISIU)

The time-frequency segments $S_m$, or the normalized/transformed time-frequency segments $\tilde{S}_m$ of the noise-free reference signal may now be used together with the corresponding noisy/processed segments $X_m$, $\tilde{X}_m$ to compute an intermediate intelligibility index $d_m$, reflecting the intelligibility of the noisy/processed signal segment $X_m$, $\tilde{X}_m$. To do so, let us first define the sample correlation coefficient d(x,y) of the elements in two K×1 vectors x and y:

$$d(x, y) = \frac{\sum_{k=1}^{K}(x(k)-\mu_x)(y(k)-\mu_y)}{\sqrt{\sum_{k=1}^{K}(x(k)-\mu_x)^2(y(k)-\mu_y)^2}}, \text{ where}$$

$$\mu_x = \frac{1}{K}\sum_{k=1}^{K} x(k) \text{ and } \mu_y = \frac{1}{K}\sum_{k=1}^{K} y(k).$$

Several options exist for computing the intermediate intelligibility index $d_m$. In particular, $d_m$ may be defined as 1) the average sample correlation coefficient of the columns in $\tilde{S}_m$ and $\tilde{X}_m$, i.e., $$d_m = \frac{1}{N}\sum_{n=1}^{N} d(\tilde{S}_m(:,n), \tilde{X}_m(:,n)),$$

or 2) the average sample correlation coefficient of the rows in $\tilde{S}_m$ and $\tilde{X}_m$, i.e., $$d_m = \frac{1}{J}\sum_{j=1}^{J} d(\tilde{S}_m(j,:)^T, \tilde{X}_m(j,:)^T),$$

or 3) the sample correlation coefficient of all elements in $\tilde{S}_m$ and $\tilde{X}_m$, i.e., $$d_m = d(\tilde{S}_m(:), \tilde{X}_m(:)),$$

where we adopted the notation $\tilde{S}_m(:)$ and $\tilde{X}_m(:)$ to represent NJ×1 vectors formed by stacking the columns of the respective matrices.

Estimation of Final Intelligibility Coefficient (FSIU)

The final intelligibility coefficient d, which reflects the intelligibility of the noisy/processed input signal x(n), is defined as the average of the intermediate intelligibility coefficients, potentially transformed via a function $u(d_m)$, across the duration of the speech-active parts of x(n), i.e., $$d = \frac{1}{M} \sum_{m=1}^{M} u(d_m).$$

The function $u(d_m)$ could for example be $$u(d_m) = \log\left(\frac{1}{1 - d_m^2}\right),$$

to link the intermediate intelligibility coefficients to information measures, but it should be clear that other choices exist.

The "do-nothing" function $u(d_m)=d_m$ is also a possible choice (it has previously been used in the STOI algorithm [3]).

In the following, a noisy/reverberant speech signal x(n) which potentially has been passed through a signal processing device, e.g. in a hearing aid, is considered. An algorithm is proposed, which can predict the average intelligibility of x(n), as perceived by a group of listeners with similar hearing profiles, e.g. normal hearing or hearing impaired listeners. To achieve this, the proposed algorithm relies on the presence of the noise-free, undistorted underlying signal s(n), see FIG. 3A. FIG. 3A shows an intrusive monaural speech intelligibility predictor unit in combination with a hearing loss model (HLM) and an evaluation unit (MSIP) (together constituting a modified monaural speech intelligibility predictor unit (MSIP')). In the embodiment of FIG. 3A, the signal x'(n) is passed through hearing loss model (HLM) configured to model the imperfections of an impaired auditory system (e.g. the impaired auditory system of a particular user). The hearing loss model unit (HLM) is e.g. based on an audiogram of an ear of a user (and possible other data related to a user's hearing ability). The hearing loss model unit (HLM) is e.g. configured to apply a frequency dependent modification of the noisy and/or processed version x' of the target signal reflecting a deviation from normal hearing, e.g. a hearing impairment, of a relevant ear of the user to provide a modified noisy and/or processed version x of the target signal for use together with the essentially noise-free version s of the target signal as inputs to the monaural speech intelligibility predictor unit (MSIP) providing the final monaural speech intelligibility predictor d. In FIG. 3A an evaluation unit (EVAL) is shown to receive and evaluate the speech intelligibility predictor d and provide a processed predictor d'. The evaluation unit (EVAL) may e.g. further process the speech intelligibility predictor value d, to e.g. graphically and/or numerically display the current and/or recent historic values, derive trends, etc. Alternatively, or additionally the evaluation unit may propose actions to the user (or a communication partner or caring person), such as add directionality, move closer, speak louder, activate SI-enhancement mode, etc. The evaluation unit may e.g. be implemented in a separate device, e.g. acting as a user interface to the speech intelligibility predictor unit (MSIP) and/or to a hearing aid including such unit, e.g. implemented as a remote control devise, e.g. as an APP of a smartphone (cf. FIG. 6A, 6B).

FIG. 3B shows an intrusive monaural speech intelligibility predictor unit (MSIP) in combination with a signal processor (SPU) and an evaluation unit (EVAL), e.g. of a hearing device. Compared to FIG. 3A, the embodiment of FIG. 3B additionally comprises a number of input units (here 2: M1, M2), e.g. microphones, for providing a time-variant electric input signal representing a sound input received at the input unit in question. At least one (such as each) of the electric input signals comprises a target signal component (e.g. a speech component) and a noise signal component (termed Noisy target in FIG. 3B). The target signal component is assumed to originate from a target signal source in the environment of the device (e.g. a hearing device, see FIG. 3C). The embodiment of FIG. 3B further comprises a configurable signal processor (SPU) for processing the electric input signals (e.g. providing beamforming and/or noise reduction, frequency and level dependent amplification, level dependent compression, or the like) and providing a processed signal x' based on one or more of the electric input signals, which are inputs to the configurable signal processor (SPU). The processed signal x' from the configurable signal processor (SPU) is fed to the hearing loss model (HLM) unit of the monaural speech intelligibility predictor unit (MSIP). The hearing loss model unit (HLM) comprises a model of a hearing loss of a user (e.g. the user of the device) and is configured to shape an input signal to provide an output signal x representing a processed (possibly hearing loss compensated) and (again) deteriorated signal, which is fed to the monaural speech intelligibility predictor (MSIP). The embodiment of FIG. 3B further comprises an antenna and transceiver unit (Rx) for receiving a wireless signal (termed Clean target in FIG. 3B) comprising the target signal and for extracting an essentially noise-free version s of the target signal, which is connected to the monaural speech intelligibility predictor (MSIP). The final speech intelligibility predictor d from the monaural speech intelligibility predictor unit (MSIP) is fed to the evaluation unit (EVAL) whose modified predictor value d' is fed to the configurable signal processor (SPU). The configurable signal processor (SPU) is adapted to control or influence the processing of the respective electric input signals based on the final speech intelligibility predictor d provided by the monaural speech intelligibility predictor unit and as modified by the evaluation unit (EVAL). The configurable signal processor (SPU) is adapted to control or influence the processing of the respective electric input signals to maximize the final speech intelligibility predictor d. (e.g. controlled by the evaluation unit (EVAL (max)).

The embodiment of FIG. 3B may e.g. further comprise an output unit for creating output stimuli configured to be perceivable by the user as sound based on an electric output either in the form of the processed signal x' from the signal processor or a signal derived therefrom. The output unit (cf. e.g. OT in FIG. 3C) may e.g. comprise a loudspeaker for placement in an ear canal of a user, or a vibrator for being attached to the skull of a user, or electrodes for placement in cochlea of a user. Thereby a hearing aid according to the present disclosure is provided. The hearing aid may take the form or an air conducting hearing instrument, a bone-conducting hearing instrument, a cochlear implant prosthesis, an active ear-protection device, a headset, an earphone with active noise cancellation, etc.

FIG. 3C shows a first embodiment of a hearing device (HD, e.g. a hearing aid) comprising an intrusive monaural speech intelligibility predictor unit (MSIP') comprising a hearing loss model part (HLM) and a predictor part (MSIP) configured to optimize a user's intelligibility (represented by index d) of an output signal u of the hearing device (HD). The embodiment of FIG. 3C is equivalent to the embodiment of FIG. 3B but further comprises an output unit comprising an output transducer (OT) in the form of a loudspeaker, which is directly connected to the output u of the signal processor (SPU). Further, the hearing aid of FIG. 3C only comprises one the input unit (IT) comprising a microphone for picking up a noisy representation y' of the target signal hearing aid and converting it to an electric input signal y, which is fed to the configurable signal processor (SPU). As in FIG. 3B, the antenna and transceiver unit (Rx) is adapted for receiving a wireless signal (termed s' in FIG. 3C) comprising the target signal and for extracting an essentially noise-free version s of the target signal, which is fed to the predictor part (MSIP) of the intrusive monaural speech intelligibility predictor unit (MSIP'). The monaural speech intelligibility predictor unit (MSIP) provides an estimate of the intelligibility of the output signal by the user in the form of the (final) speech intelligibility predictor d, which is fed to a control part of the configurable signal processor (SPU) to modify signal processing to optimize d. in a feedback loop.

Figure 4A:
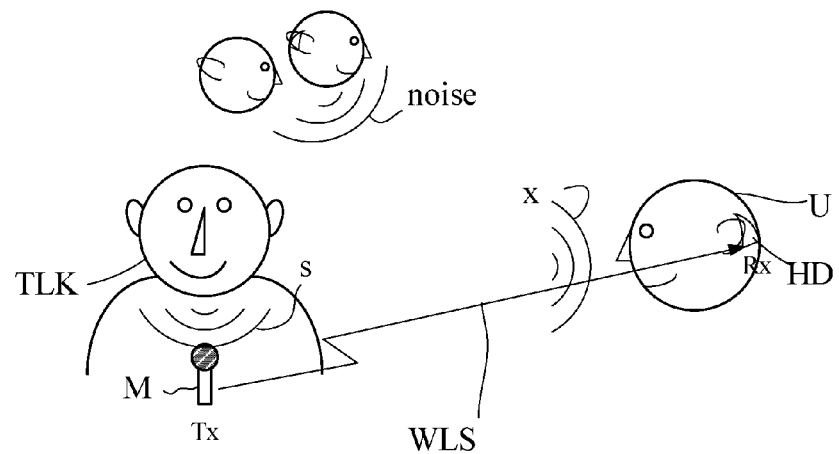
FIG. 4A shows a first scenario for using a hearing aid comprising an intrusive monaural speech intelligibility predictor according to the present disclosure to improve a hearing aid user's intelligibility of speech from a speaker wearing a wireless microphone (e.g. in a teaching or lecture situation)

FIG. 4A shows a first scenario for using a hearing aid (HD) comprising an intrusive monaural speech intelligibility predictor according to the present disclosure (as described in connection with FIG. 2A, 2B, 2C and FIG. 3A, 3B, 3C above) to improve a hearing aid user's (U) intelligibility of speech from a speaker (TLK) wearing a wireless microphone (M), e.g. in a teaching or lecture situation. The speaker's voice (the target signal) is picked up by the microphone (M) located close to the speaker's mouth. The microphone (M) comprises a transmitter (Tx) for wirelessly transmitting the essentially noise-free version of the target signal s to a corresponding receiver (Rx) of the hearing aid worn by the user (U) using wireless link WLS (e.g. using FM or Bluetooth or other standardized or proprietary technology). Simultaneously, an acoustically propagated version of the target signal coloured (modified) by the location (e.g. a room with reflecting surfaces, e.g. walls) and mixed with possible noise (noise) from the environment is picked up (noisy signal x) by one or more microphone of the hearing aid (HD).

Figure 4B:
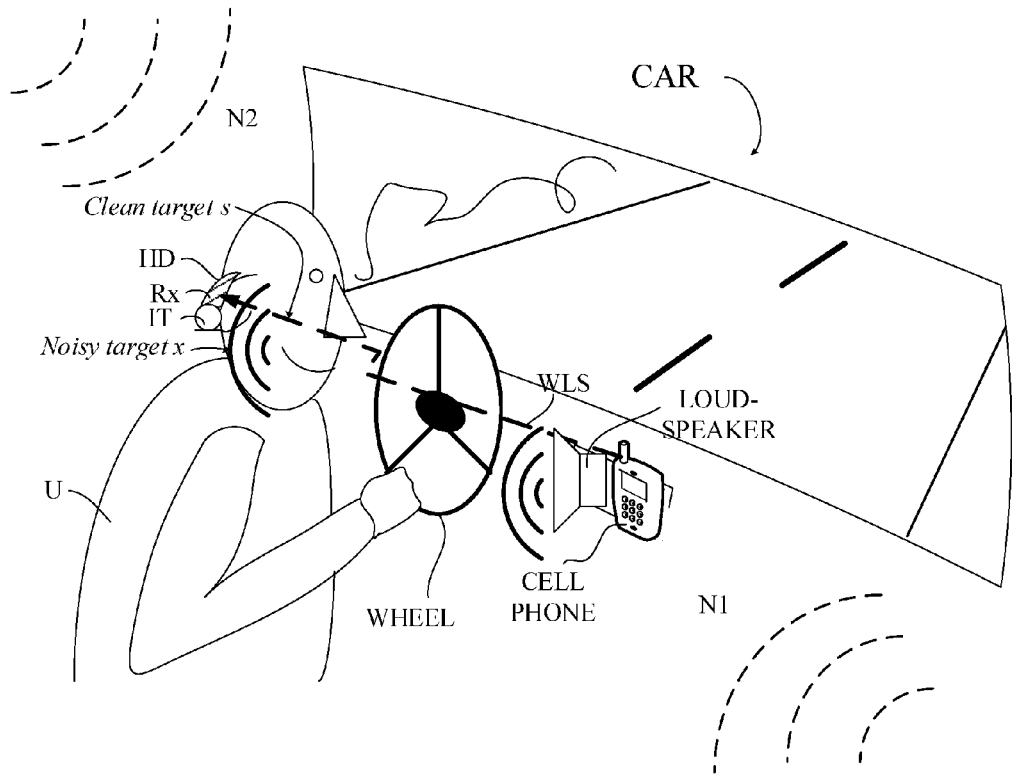
FIG. 4B shows a second scenario for using a hearing aid comprising an intrusive monaural speech intelligibility predictor according to the present disclosure to improve a hearing aid user's intelligibility of speech from a remote speaker of a telephone conversation using a handsfree telephone set in a car, where remote sound is wirelessly as well as acoustically transmitted to the hearing aid user.

FIG. 4B shows a second (similar) scenario for using a hearing aid (HD) comprising an intrusive monaural speech intelligibility predictor according to the present disclosure to improve a hearing aid user's (U) intelligibility of speech from a remote speaker of a telephone conversation using a handsfree telephone set in a car (CAR), where remote sound is wirelessly as well as acoustically transmitted to the hearing aid user. The 'clean' target signal of the remote speaker received by the telephone (CELL PHONE) is wirelessly transmitted to and received by a receiver (Rx) of the hearing aid (HD) as clean signal s (Clean target s in FIG. 4B), while the sound is simultaneously propagated to a microphone (IT) of the hearing aid by a loudspeaker (LOUDSPEAKER) of the handsfree telephone set providing 'noisy signal' x (Noisy target x in FIG. 4B). The user is driving a car (CAR, WHEEL) while talking in a telephone via a handsfree telephone set. The noise in the car cabin (indicated by noise sources N1, N2) is acoustically mixed with the 'target signal' played by a loudspeaker of the handsfree telephone set (or of the telephone itself) and picked up as noisy target signal x, by the hearing aid microphone(s) (IT).

The hearing aid (HD) used in the two scenarios of FIG. 4A, 4B may be a hearing aid according to the present disclosure, e.g. as described in connection with FIG. 3A, 3B, 3C, which is configured to adapt the processing of an acoustic signal picked up by a microphone of the hearing aid and processed by a signal processing device to optimize the user's speech intelligibility (based on a predictor of a monaural speech intelligibility predictor unit, as proposed by the present disclosure).

Figure 5A:
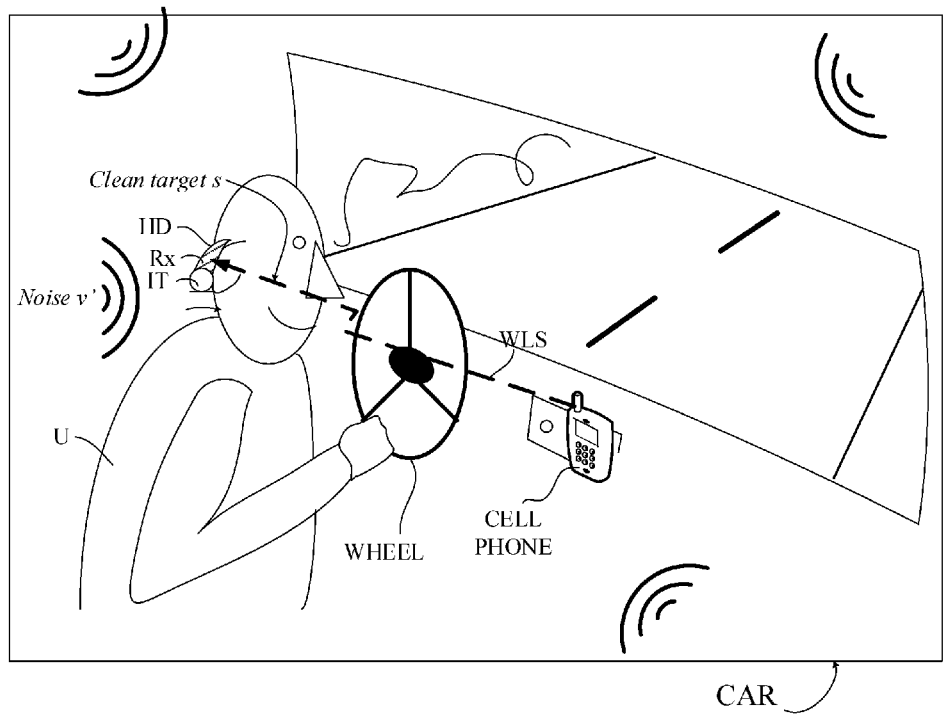
FIG. 5A shows a third scenario for using a hearing aid comprising an intrusive monaural speech intelligibility predictor according to the present disclosure to improve a hearing aid user's intelligibility of speech from a remote speaker of a telephone conversation using a handsfree telephone set in a car, where remote sound is (only) wirelessly transmitted to the hearing aid user.

FIG. 5A shows a third scenario for using a hearing aid (HD) comprising an intrusive monaural speech intelligibility predictor according to the present disclosure to improve a hearing aid user's intelligibility of speech from a remote speaker of a telephone conversation using a handsfree telephone set in a car (CAR, WHEEL), where sound from a remote communication partner is wirelessly transmitted to the hearing aid user (U). The scenario of FIG. 5A is similar to the scenario of FIG. 4B apart from the fact that in the scenario of FIG. 5A the voice of the remote communication partner is NOT played by a loudspeaker in the car.

The clean target signal s is transmitted from the CELL PHONE to the hearing aid HD. The background noise v' (Noise v') of the car cabin is captured by the microphone(s) (IT) of the hearing aid. It can be assumed that the background noise v' as captured is substantially equal to the noise $v_{ed}$ (Noise $v_{ed}$) that is present at the ear drum (Ear drum) of the user (cf. FIG. 5B, 5C). The assumption is of course better the closer to the ear drum the microphone is situated (and/or the more open the ear canal part is). In an embodiment, a microphone of the hearing aid is located in the ear canal, e.g. at the entrance of the ear canal or close to the ear drum (cf. e.g. $IT_3$ in FIG. 5C).

Figure 5B:
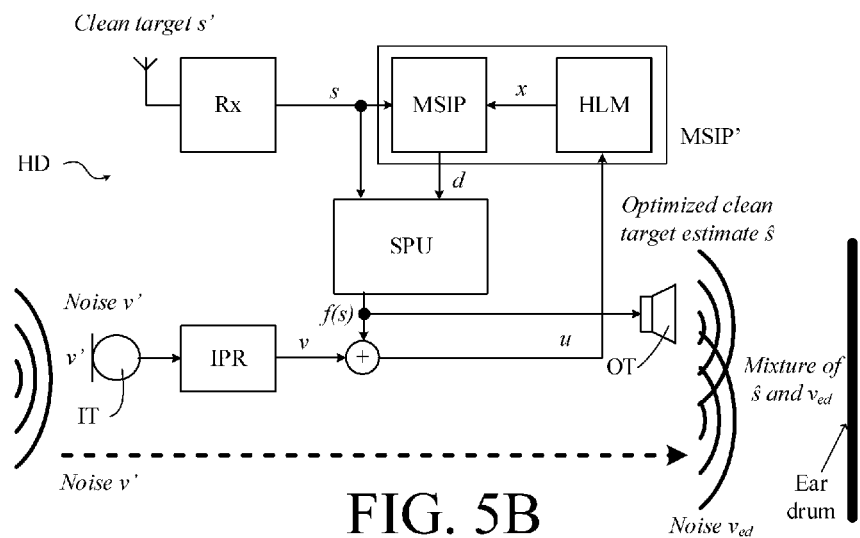
FIG. 5B shows an embodiment of a hearing aid comprising an intrusive monaural speech intelligibility predictor for use in the (third) scenario of FIG. 5A.
Figure 5C:
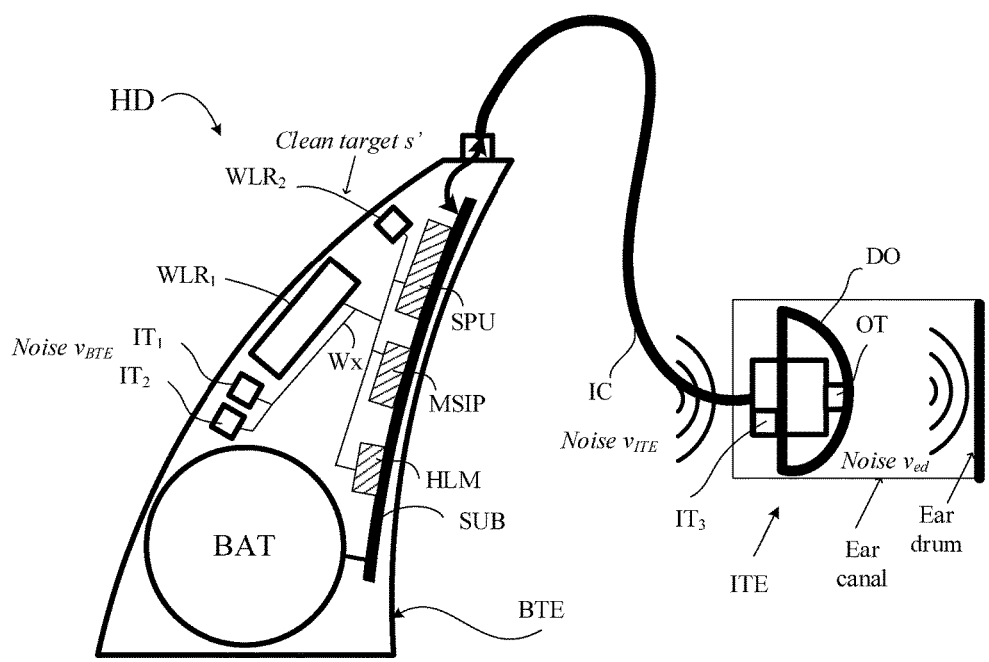
FIG. 5C illustrates an exemplary hearing aid formed as a receiver in the ear (RITE) type of hearing aid comprising a part adapted for being located behind pinna and a part comprising an output transducer (e.g. a loudspeaker/receiver) adapted for being located in an ear canal of the user.

FIG. 5B shows an embodiment of a hearing aid comprising an intrusive monaural speech intelligibility predictor for use in the (third) scenario of FIG. 5A. The embodiment of a hearing aid (HD) shown in FIG. 5B comprises the same functional components as the embodiment shown in FIG. 3C. The interconnection of the signal processor (SPU) and the wireless receiver (Rx) and the input transducer (IT) is different, however. As shown in FIG. 5A and as indicated in FIGS. 5B and 5C, the sound output of the loudspeaker (OT) of the hearing aid, equal to the processed signal $f(s)$ from the signal processor (SPU), is acoustically mixed with 'environmental' (car cabin) noise v, at the eardrum (Ear drum, cf. Mixture of s and $v_{ed}$ in FIG. 5B).

The basic idea of the embodiment of a hearing aid in FIG. 5B is to process the clean version s of the target signal so that the speech intelligibility d is maximized when the processed version of the clean target signal ($f(s)$). The processed version of the clean target signal ($f(s)$) can be adaptively controlled, whereas this is not the case for the car cabin noise $v_{ed}$ at the eardrum (which is given).

Using a model of speech intelligibility (e.g. as disclosed in the present disclosure) in the configuration of FIG. 5B, an estimate of a user's intelligibility of speech components present in the processed signal $f(s)$ from the signal processor (SPU), when presented to the ear by a loudspeaker (or an acoustic guide element of the hearing aid) and mixed with the noise signal $v_{ed}$ present at the ear drum, can be determined, cf. signal $u=f(s)+v$, which is used as the 'processed/noisy target signal input' to the hearing loss model (HLM) of the monaural speech intelligibility predictor unit (MSIP') in FIG. 5B.

Preferably, the loudspeaker (or alternatively an acoustic guide element) is located in the ear canal, preferably close to the ear drum to deliver the processed signal $f(s)$ to the ear drum. Preferably, the microphone(s) of the hearing device, which is(are) used to pick up background noise v' (cf. FIG. 5A, 5B), is(are) located close to the ear drum, or at the entrance of the ear canal, or in pinna, or behind the ear. In an embodiment, the noise signal picked up by a given microphone is appropriately modified (in the hearing aid) to account for a transfer function for an acoustic signal from the location of the microphone to the ear drum to thereby give a better estimate of the background noise $v_{ed}$ received by the user (at the ear drum) for use in the estimate of the speech intelligibility $d=d(f(s)+v,s)$.

In the configuration of FIG. 5B, the signal processor (SPU) is configured to iteratively modify signal processing of the clean target signal s received from wireless receiver unit (Rx) to provide processed version $f(s)$ the clean target signal s that optimizes speech intelligibility of the (mixed) signal present at the ear drum of the user (in practice here approximated by maximizing the monaural speech intelligibility predictor $d(f(s)+v,s)$ according to the resent disclosure).

As an alternative to using a speech intelligibility predictor to modify (optimize) s (or as an extreme option of the present disclosure), a simple increase of gain of the clean target signal s (i.e. f(s)=g's, g being a gain factor, e.g. g=10) may be used to increase the signal to noise ratio (SNR) at the ear drum (assuming a constant level of the background (cabin) noise $v_{ed}$ at the ear drum). In practice, such reliance only on increasing gain of the clean target signal may, however, not be attractive or possible (e.g. due to acoustic feedback problems, maximum power output limitations of the loudspeaker, or uncomfortable levels of the user, etc.). Instead an appropriate frequency dependent shaping of the clean target signal is generally proposed and governed by the monaural speech intelligibility predictor (including the hearing loss model (HLM) preferably defining decisive aspects of a hearing impairment of the user of the hearing aid).

FIG. 5C illustrates an exemplary hearing aid (HD) formed as a receiver in the ear (RITE) type of hearing aid comprising a part (BTE) adapted for being located behind pinna and a part (ITE) comprising an output transducer (OT, e.g. a loudspeaker/receiver) adapted for being located in an ear canal (Ear canal) of the user (e.g. exemplifying a hearing aid (HD) as shown in FIG. 5A, 5B). The BTE-part (BTE) and the ITE-part (ITE) are connected (e.g. electrically connected) by a connecting element (IC). In the embodiment of a hearing aid of FIG. 5C, the BTE part (BTE) comprises two input units comprising two (individually selectable) input transducers (e.g. microphones) ($IT_1$, $IT_2$) each for providing an electric input audio signal representative of an input sound signal from the environment (in the scenario of FIG. 5A, from the car cabin). The hearing device of FIG. 5C further comprises two (individually selectable) wireless receivers ($WLR_1$, $WLR_2$) for providing respective directly received auxiliary audio and/or information signals. The hearing aid (HD) further comprises a substrate (SUB) whereon a number of electronic components are mounted, including a configurable signal processor (SPU), a monaural speech intelligibility predictor unit (MSIP), and a hearing loss model unit (HLM, coupled to each other and input and output units via electrical conductors Wx). The configurable signal processor (SPU) provides an enhanced audio signal (cf. signal $f(s)$ in FIG. 5B), which is intended to be presented to a user. In the embodiment of a hearing aid device in FIG. 5C, the ITE part (ITE) comprises an output unit in the form of a loudspeaker (receiver) (OT) for converting an electric signal ($f(s)$ in FIG. 5B) to an acoustic signal. The ITE-part further comprises an input unit comprising an input transducer (e.g. a microphone) ($IT_3$) for providing an electric input audio signal representative of an input sound signal from the environment in the ear canal (here approximating the noise $v_{ed}$ from the car cabin at the ear drum (Ear drum) of the user (U) wearing the hearing aid (HD)). In other embodiments, the hearing aid may comprise only the input unit ($IT_3$) located in or at the ear canal, or the input unit ($IT_3$) located in or at the ear canal in combination with a an input unit located elsewhere, e.g. in a BTE-part. The ITE-part further comprises a guiding element, e.g. a dome, (DO) for guiding and positioning the ITE-part in the ear canal of the user.

The hearing aid (HD) exemplified in FIG. 5C is a portable device and further comprises a battery (BAT) for energizing electronic components of the BTE- and ITE-parts.

In an embodiment, the hearing aid (HD) comprises a directional microphone system (beamformer) adapted to enhance a target acoustic source among a multitude of acoustic sources in the local environment of the user wearing the hearing aid device. In an embodiment, the directional system is adapted to detect (such as adaptively detect) from which direction a particular part of the microphone signal originates.

Figure 7:
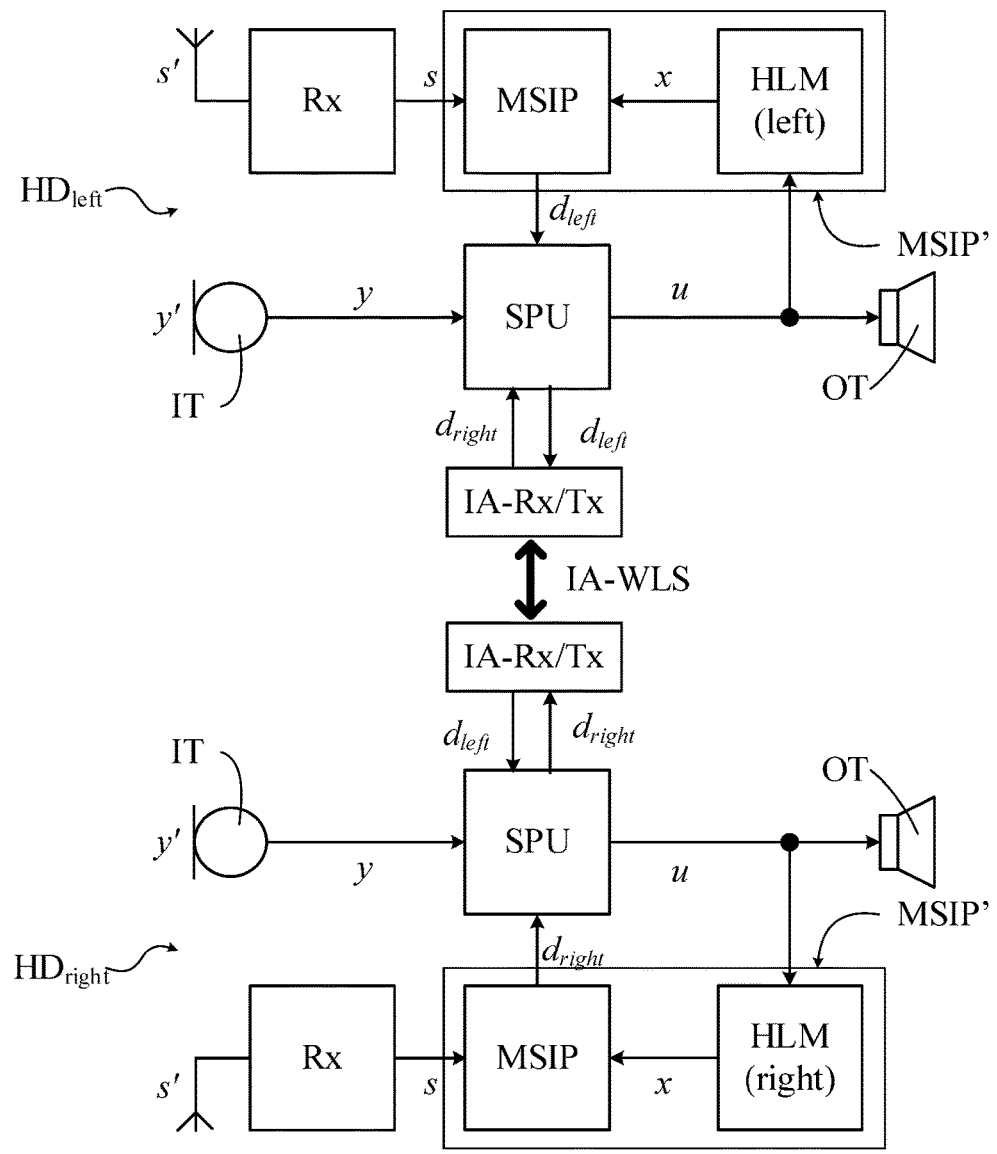
FIG. 7 shows an embodiment of a binaural hearing aid system according to the present disclosure comprising a left and right hearing devices, each comprising a monaural speech intelligibility predictor whose individual predictor values $d_{left}$ and $d_{right}$ are exchanged between the hearing devices and used to influence or control signal processing in the hearing devices to optimize binaural speech intelligibility of the user.

The hearing aid of FIG. 5C may form part of a hearing aid and/or a binaural hearing aid system according to the present disclosure (cf. e.g. FIG. 7).

Figure 6A:
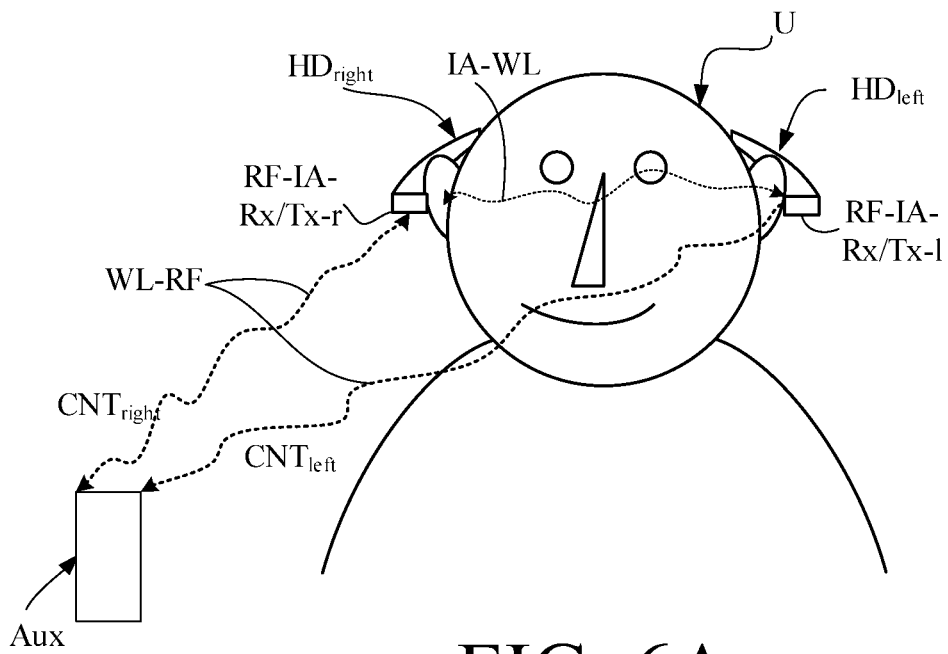
FIG. 6A shows a binaural hearing aid system according to the present disclosure comprising first and second hearing aids and an auxiliary device.
Figure 6B:
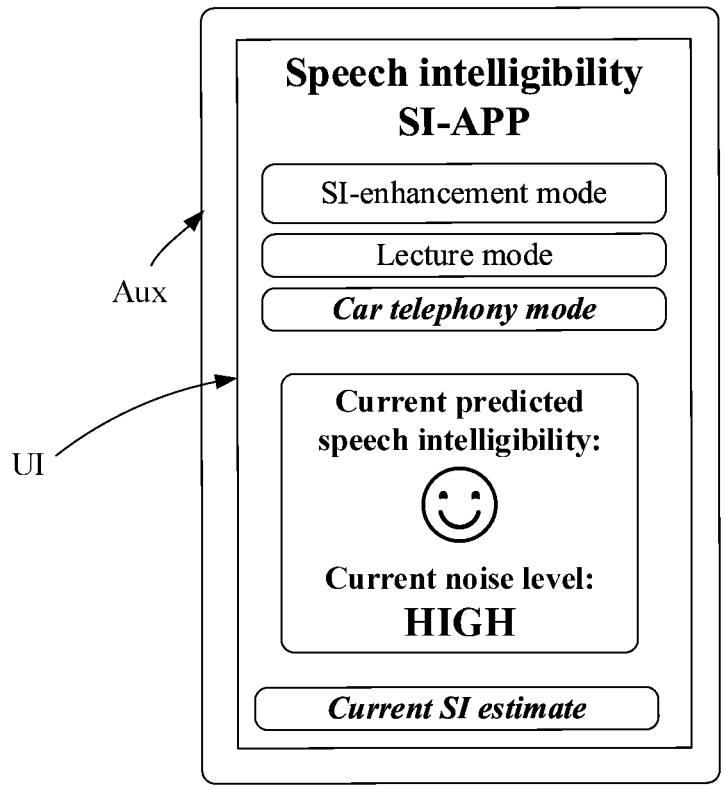
FIG. 6B shows the auxiliary device comprising a user interface in the form of an APP for controlling and displaying data related to the speech intelligibility predictors.

FIG. 6A shows an embodiment of a binaural hearing system comprising left and right hearing devices ($HD_{left}$, $HD_{right}$), e.g. hearing aids, in communication with a portable (handheld) auxiliary device (Aux) functioning as a user interface (UI) for the binaural hearing aid system (cf. FIG. 6B). In an embodiment, the binaural hearing system comprises the auxiliary device (Aux, and the user interface UI). In the embodiment of FIG. 6A, wireless links denoted IA-WL (e.g. an inductive link between the left and right hearing devices) and WL-RF (e.g. RF-links (e.g. Bluetooth) between the auxiliary device Aux and the left $HD_{left}$, and between the auxiliary device Aux and the right $HD_{right}$, hearing aid, respectively) are indicated (implemented in the devices by corresponding antenna and transceiver circuitry, indicated in FIG. 6A in the left and right hearing devices as RF-IA-Rx/Tx-l and RF-IA-Rx/Tx-r, respectively).

FIG. 6B shows the auxiliary device (Aux) comprising a user interface (UI) in the form of an APP for controlling and displaying data related to the speech intelligibility predictors. The user interface (U) comprises a display (e.g. a touch sensitive display) displaying a screen of a Speech intelligibility SI-APP for controlling the hearing aid system and presenting information to the user. The APP comprises a number of predefined action buttons regarding functionality of the binaural (or monaural) hearing system. In the exemplified (part of the) APP, a user (U) has the option of influencing a mode of operation via the selection of a SI-prediction mode to be a Monaural SIP or Binaural SIP mode. In the screen shown in FIG. 10B, the un-shaded buttons are selected, i.e. SI-enhancement mode (where the processing is adapted to optimize speech intelligibility based on the (monaural or binaural) speech intelligibility predictor) together with a specific Car telephony mode (as described in connection with FIG. 5A, 5B, 5C). Further, a show Current SI-estimate has been activated (resulting in a current predicted value of the binaural speech intelligibility predictor being displayed (in the form of the positive indicator '☺') together with an indication of the current noise level (indicated as 'HIGH')). The grey shaded button Lecture mode (as described in connection with FIG. 4A, 4B) may be selected instead of Car telephony mode.

FIG. 7 shows an embodiment of a binaural hearing aid system according to the present disclosure comprising a left and right hearing devices ($HD_{left}$, $HD_{right}$), each comprising a monaural speech intelligibility predictor unit (MSIP') whose individual predictor values di and $d_{right}$ are exchanged between the hearing devices and used to influence or control signal processing of respective signal processors (SPU) in the hearing devices to optimize binaural speech intelligibility of the user. The left and right hearing devices ($HD_{left}$, $HD_{right}$), are e.g. hearing devices as shown in an discussed in connection with FIG. 3C. Each of the left and right hearing aids comprises antenna and transceiver circuitry (IA-Rx/Tx) for allowing a communication link (IA-WLS) to be established and information ($d_{left}$, $d_{right}$) to be exchanged between said left and right hearing aids. In an embodiment, the binaural hearing aid system comprises a binaural speech intelligibility prediction unit for providing a final binaural speech intelligibility measure $d_{binaural}$ of the predicted speech intelligibility of the user when exposed to a sound input, wherein the final binaural speech intelligibility measure $d_{binaural}$ is determined in dependence of the final monaural speech intelligibility predictor values $d_{left}$, $d_{right}$ of the respective left and right hearing aids. The binaural speech intelligibility prediction unit may e.g. be implemented in one or both of the signal processors (SPU) of the left and right hearing devices. In an embodiment, the final binaural speech intelligibility measure $d_{binaural}$ is determined as the maximum of the speech intelligibility predictor values $d_{left}$, $d_{right}$ of the respective left and right hearing aids: $d_{binaural} = \max(d_{left}, d_{right})$.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein.

Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[1] American National Standards Institute, "ANSI S3.5, Methods for the Calculation of the Speech Intelligibility Index," New York 1995.
[2] K. S. Rhebergen and N. J. Versfeld, "A speech intelligibility index based approach to predict the speech reception threshold for sentences in fluctuating noise for normal-hearing listeners," J. Acoust. Soc. Am., vol. 117, no. 4, pp. 2181-2192, 2005.
[3] C. H. Taal, R. C. Hendriks, R. Heusdens, and J. Jensen, "An Algorithm for Intelligibility Prediction of Time-Frequency Weighted Noisy Speech." IEEE Trans. Audio, Speech, Lang. Process., vol. 19, no. 7, pp. 2125-2136, September 2011.
[4] B. C. J. Moore, "Cochlear Hearing Loss," Physiological, Psychological and Technical Issues, "Wiley, 2007.
[5] R. Beutelmann and T. Brand, "Prediction of intelligibility in spatial noise and reverberation for normal-hearing and hearing-impaired listeners," J. Acoust. Soc. Am., Vol. 120, no. 1, pp. 331-342, April 2006.

The invention claimed is:

1. A monaural speech intelligibility predictor unit configured to receive a target signal comprising speech in a noise-free version s and in a noisy and/or processed version x, the monaural speech intelligibility predictor unit being further configured to provide as an output a final monaural speech intelligibility predictor value d indicative of a listener's perception of said noisy and/or processed version x of the target signal, the monaural speech intelligibility predictor unit comprising:

a first input unit for providing a time-frequency representation s(k,m) of said noise-free version s of the target signal, k being a frequency bin index, k=1, 2, ..., K, and m being a time index;

a second input unit for providing a time-frequency representation x(k,m) of said noisy and/or processed version x of the target signal, k being a frequency bin index, k=1, 2, ..., K, and m being a time index;

a first envelope extraction unit for providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, ..., J, and m being the time index;

a second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, ..., J, and m being the time index;

a first time-frequency segment division unit for dividing said time-frequency sub-band representation $s_j(m)$ of the noise-free version s of the target signal into time-frequency segments $S_m$ corresponding to a number N of successive samples of said sub-band signals;

a second time-frequency segment division unit for dividing said time-frequency sub-band representation $x_j(m)$ of the noisy and/or processed version x of the target signal into time-frequency segments $X_m$ corresponding to a number N of successive samples of said sub-band signals;

a normalization and transformation unit configured to provide at least one normalization and/or transformation operation of rows and at least one normalization and/or transformation operation of columns of the time-frequency segments $S_m$ and $X_m$;

an intermediate speech intelligibility calculation unit configured to provide intermediate speech intelligibility coefficients $d_m$ estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$; and a final monaural speech intelligibility calculation unit for calculating the final monaural speech intelligibility predictor d estimating an intelligibility of said noisy and/or processed version x of the target signal by combining, e.g. by averaging, or by applying a MIN or MAX-function to, said intermediate speech intelligibility coefficients $d_m$, or a transformed version thereof, over time, wherein said first and second time-frequency segment division units are configured to divide said time-frequency representations $s_j(m)$ and $x_j(m)$, respectively, into segments in the form of spectrograms corresponding to N successive samples of all sub-band signals, wherein the $m^{th}$ segment is defined by the JxN matrix $$Z_m = \begin{bmatrix} z_1(m-N+1) & \ldots & z_1(m) \\ \ldots & \ldots & \ldots \\ z_j(m-B+1) & \ldots & z_J(m) \end{bmatrix},$$

where z (Z) represents s (S) or x (X).

2. A monaural speech intelligibility predictor unit according to claim 1 comprising:

a voice activity detector unit for indicating whether or not, or to what extent, a given time-segment of the noise-free version s and the noisy and/or processed version x, respectively, of the target signal comprises or is estimated to comprise speech, and providing a voice activity control signal indicative thereof.

3. A monaural speech intelligibility predictor unit according to claim 1 comprising:

a voice activity detector unit for identifying time-segments of the noise-free version s and the noisy and/or processed version x, respectively, of the target signal comprising or estimated to comprise speech, and wherein the monaural speech intelligibility predictor unit is configured to provide modified versions of the noise-free version s and of the noisy and/or processed version x, respectively, of the target signal, said modified versions comprising only such time segments comprising speech or being estimated to comprise speech.

4. A monaural speech intelligibility predictor unit according to claim 1 comprising:

a hearing loss model unit configured to apply a modification of the said noisy and/or processed version x of the target signal reflecting a deviation from normal hearing of a relevant ear of the listener to provide a modified noisy and/or processed version x of the target signal for use together with said noise-free version s of the target signal as a basis for calculating the final monaural speech intelligibility predictor d.

5. A monaural speech intelligibility predictor unit configured to receive a target signal comprising speech in a noise-free version s and in a noisy and/or processed version x, the monaural speech intelligibility predictor unit being further configured to provide as an output a final monaural speech intelligibility predictor value d indicative of a listener's perception of said noisy and/or processed version x of the target signal, the monaural speech intelligibility predictor unit comprising:

a first input unit for providing a time-frequency representation s(k,m) of said noise-free version s of the target signal, k being a frequency bin index, k=1, 2, . . . , K, and m being a time index;

a second input unit for providing a time-frequency representation x(k,m) of said noisy and/or processed version x of the target signal, k being a frequency bin index, k=1, 2, . . . , K, and m being a time index;

a first envelope extraction unit for providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, . . . , J, and m being the time index;

a second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, . . . , J, and m being the time index;

a first time-frequency segment division unit for dividing said time-frequency sub-band representation s of the noise-free version s of the target signal into time-frequency segments $S_m$ corresponding to a number N of successive samples of said sub-band signals;

a second time-frequency segment division unit for dividing said time-frequency sub-band representation $x_j(m)$ of the noisy and/or processed version x of the target signal into time-frequency segments $X_m$ corresponding to a number N of successive samples of said sub-band signals;

a normalization and transformation unit configured to provide at least one normalization and/or transformation operation of rows and at least one normalization and/or transformation operation of columns of the time-frequency segments $S_m$ and $X_m$;

an intermediate speech intelligibility calculation unit configured to provide intermediate speech intelligibility coefficients $d_m$ estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$;

a final monaural speech intelligibility calculation unit for calculating the final monaural speech intelligibility predictor d estimating an intelligibility of said noisy and/or processed version x of the target signal by combining, e.g. by averaging, or by applying a MIN or MAX-function to, said intermediate speech intelligibility coefficients $d_m$, or a transformed version thereof, over time; and a hearing loss model unit configured to apply a modification of the said noisy and/or processed version x of the target signal reflecting a deviation from normal hearing of a relevant ear of the listener to provide a modified noisy and/or processed version x of the target signal for use together with said noise-free version s of the target signal as a basis for calculating the final monaural speech intelligibility predictor d, wherein said hearing loss model unit is configured to add a statistically independent noise signal, which is spectrally shaped according to an audiogram of the relevant ear of the listener, to said noisy and/or processed version x of the target signal.

6. A monaural speech intelligibility predictor unit according to claim 1 configured to extract said temporal envelope signals $x_j(m)$ and $s_j(m)$, respectively, as $$z_j(m) = f\left(\sqrt{\sum_{k=k1(j)}^{k2(j)} |z(k,m)|^2}\right),$$

where z represents x or s, j=1, ..., J and m=1, ..., M, k1(j) and k2(j) denote DFT bin indices corresponding to lower and higher cut-off frequencies of the $j^{th}$ sub-band, J is the number of sub-bands, and M is the number of signal frames in the signal in question, and $f(\bullet)$ is a function.

7. A monaural speech intelligibility predictor unit configured to receive a target signal comprising speech in a noise-free version s and in a noisy and/or processed version x, the monaural speech intelligibility predictor unit being further configured to provide as an output a final monaural speech intelligibility predictor value d indicative of a listener's perception of said noisy and/or processed version x of the target signal, the monaural speech intelligibility predictor unit comprising:

a first input unit for providing a time-frequency representation s(k,m) of said noise-free version s of the target signal, k being a frequency bin index, k=1, 2, ..., K, and m being a time index;

a second input unit for providing a time-frequency representation x(k,m) of said noisy and/or processed version x of the target signal, k being a frequency bin index, k=1, 2, ..., K, and m being a time index;

a first envelope extraction unit for providing a time-frequency sub-band representation $s_j(m)$ of the noise-free version s of the target signal representing temporal envelopes, or functions thereof, of frequency sub-band signals of said noise-free target signal, j being a frequency sub-band index, j=1, 2, ..., J, and m being the time index;

a second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, ..., J, and m being the time index;

a first time-frequency segment division unit for dividing said time-frequency sub-band representation $s_j(m)$ of the noise-free version s of the target signal into time-frequency segments $S_m$ corresponding to a number N of successive samples of said sub-band signals;

a second time-frequency segment division unit for dividing said time-frequency sub-band representation $x_j(m)$ of the noisy and/or processed version x of the target signal into time-frequency segments $X_m$ corresponding to a number N of successive samples of said sub-band signals;

a normalization and transformation unit configured to provide at least one normalization and/or transformation operation of rows and at least one normalization and/or transformation operation of columns of the time-frequency segments $S_m$ and $X_m$;

an intermediate speech intelligibility calculation unit configured to provide intermediate speech intelligibility coefficients $d_m$ estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$; and a final monaural speech intelligibility calculation unit for calculating the final monaural speech intelligibility predictor d estimating an intelligibility of said noisy and/or processed version x of the target signal by combining, e.g. by averaging, or by applying a MIN or MAX-function to, said intermediate speech intelligibility coefficients $d_m$, or a transformed version thereof, over time;

wherein said temporal envelope signals $x_j(m)$ and $s_j(m)$, respectively, are extracted as $$z_j(m) = f\left(\sqrt{\sum_{k=k1(j)}^{k2(j)} |z(k,m)|^2}\right),$$

where represents x or s, j=1, ..., J and m=1, ..., M, k1(j) and k2(j) denote DFT bin indices corresponding to lower and higher cut-off frequencies of the $j^{th}$ sub-band, J is the number of sub-bands, and M is the number of signal frames in the signal in question, and $f(\bullet)$ is a function, and wherein the function $f(\bullet)=f(w)$, where w represents $$\left(\sqrt{\sum_{k=k1(j)}^{k2(j)} |z(k,m)|^2}\right),$$

is selected among the following functions
$f(w)=w$ representing the identity
$f(w)=w^2$ providing power envelopes,
$f(w)=2 \cdot \log w$ or $f(w)=w^\beta$, $0<\beta<2$, allowing the modelling of the compressive non-linearity of the healthy cochlea, or combinations thereof.

8. A monaural speech intelligibility predictor unit according to claim 1 comprising a first normalization and/or transformation unit configured to providing normalized and/or transformed versions $\tilde{S}_m$ of said time-frequency segments $S_m$;

a second normalization and/or transformation unit configured to providing normalized and/or transformed versions $\tilde{X}_m$ of said time-frequency segments $X_m$.

9. A monaural speech intelligibility predictor unit configured to receive a target signal comprising speech in a noise-free version s and in a noisy and/or processed version x, the monaural speech intelligibility predictor unit being further configured to provide as an output a final monaural speech intelligibility predictor value d indicative of a listener's perception of said noisy and/or processed version x of the target signal, the monaural speech intelligibility predictor unit comprising:
- a first input unit for providing a time-frequency representation s(k,m) of said noise-free version s of the target signal, k being a frequency bin index, k=1, 2, ..., K, and m being a time index;
- a second input unit for providing a time-frequency representation x(k,m) of said noisy and/or processed version x of the target signal, k being a frequency bin index, k=1, 2, ..., K, and m being a time index;
- a first envelope extraction unit for providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, ..., J, and m being the time index;
- a second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, ..., J, and m being the time index;
- a first time-frequency segment division unit for dividing said time-frequency sub-band representation $s_j(m)$ of the noise-free version s of the target signal into time-frequency segments $S_m$ corresponding to a number N of successive samples of said sub-band signals;
- a second time-frequency segment division unit for dividing said time-frequency sub-band representation $x_j(m)$ of the noisy and/or processed version x of the target signal into time-frequency segments $X_m$ corresponding to a number N of successive samples of said sub-band signals;
- a normalization and transformation unit configured to provide at least one normalization and/or transformation operation of rows and at least one normalization and/or transformation operation of columns of the time-frequency segments $S_m$ and $X_m$;
- an intermediate speech intelligibility calculation unit configured to provide intermediate speech intelligibility coefficients $d_m$ estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$;
- a final monaural speech intelligibility calculation unit for calculating the final monaural speech intelligibility predictor d estimating an intelligibility of said noisy and/or processed version x of the target signal by combining, e.g. by averaging, or by applying a MIN or MAX-function to, said intermediate speech intelligibility coefficients $d_m$, or a transformed version thereof, over time;
- a first normalization and/or transformation unit configured to providing normalized and/or transformed versions $\tilde{S}_m$ of said time-frequency segments $S_m$; and
- a second normalization and/or transformation unit configured to providing normalized and/or transformed versions $\tilde{X}_m$ of said time-frequency segments $X_m$,
- wherein first and second normalization and/or transformation units are configured to apply one or more of the following algorithms to the time-frequency segments $X_m$ and $S_m$, respectively, commonly denoted $Z_m$, where sub-script, time index m is skipped for simplicity in the following expressions:

normalization of rows to zero mean:

$$g_1(Z)=Z-\mu_z^r 1^T,$$

where $\mu_z^r$ is a J×1 vector whose j'th entry is the mean of the j'th row of Z, hence the superscript r in $\mu_z^r$, where 1 denotes an N×1 vector of ones, and where superscript T denotes matrix transposition;

normalization of rows to unit-norm:

$$g_2(Z)=D^r(Z)Z,$$

where $D^r(Z)=\text{diag}([1/\sqrt{Z(1,:)Z(1,:)^H} \Lambda 1/\sqrt{Z(J,:)Z(J,:)^H}])$, where diag(•) is a diagonal matrix with the elements of the arguments on the main diagonal, and where Z(j,:) denotes the j'th row of Z, such that $D^r(Z)$ is a J×J diagonal matrix with the inverse norm of each row on the main diagonal, and zeros elsewhere, the superscript H denotes Hermitian transposition, and pre-multiplication with $D^r(Z)$ normalizes the rows of the resulting matrix to unit-norm;

fourier transformation applied to each row $$g_3(Z)=ZF,$$

where F is an N×N Fourier matrix;

fourier transformation applied to each row followed by computing the magnitude of the resulting complex-valued elements $$g_4=|ZF|$$

where |•| computes the element-wise magnitudes;

the identity operator $$g_5(Z)=Z,$$

normalization of columns to zero mean:

$$h_1(Z)=Z-1\mu_z^{c\,T},$$

where $\mu_z^c$ is a N×1 vector whose $i^{th}$ entry is the mean of the $i^{th}$ row of Z, and where 1 denotes a J×1 vector of ones;

normalization of columns to unit-norm:

$$h_2(Z)=ZD^c(Z),$$

where $D^c(Z)=\text{diag}([1/\sqrt{Z(:,1)^H Z(:,1)} \Lambda 1/\sqrt{Z(:,N)^H Z(:,N)}])$, where Z(:, n) denotes the n'th row of Z, such that $D^c(z)$ is a diagonal N×N matrix with the inverse norm of each column on the main diagonal, and zeros elsewhere, and where a post-multiplication with $D^c(Z)$ normalizes the rows of the resulting matrix to unit-norm.

10. A monaural speech intelligibility predictor unit according to claim 1 wherein the intermediate speech intelligibility calculation unit is configured to determine said intermediate speech intelligibility coefficients $d_m$ in dependence on a, e.g. linear, sample correlation coefficient d(a,b) of the elements in two K×1 vectors a and b, d(a,b) being defined by:

$$d(a,b) = \frac{\sum_{k=1}^{K}(a(k)-\mu_a)(b(k)-\mu_b)}{\sqrt{\sum_{k=1}^{K}(a(k)-\mu_a)^2(b(k)-\mu_b)^2}}, \text{ where}$$

$$\mu_a = \frac{1}{K}\sum_{k=1}^{K}a(k) \text{ and}$$

$$\mu_b = \frac{1}{K}\sum_{k=1}^{K}b(k),$$

where k is the index of the vector entry and K is the vector dimension.

11. A monaural speech intelligibility predictor unit configured to receive a target signal comprising speech in a noise-free version s and in a noisy and/or processed version x, the monaural speech intelligibility predictor unit being further configured to provide as an output a final monaural speech intelligibility predictor value d indicative of a listener's perception of said noisy and/or processed version x of the target signal, the monaural speech intelligibility predictor unit comprising:

a first input unit for providing a time-frequency representation s(k,m) of said noise-free versions of the target signal, k being a frequency bin index, k=1, 2, ..., K, and m being a time index;

a second input unit for providing a time-frequency representation x(k,m) of said noisy and/or processed version x of the target signal, k being a frequency bin index, k=1, 2, ..., K, and m being a time index;

a first envelope extraction unit for providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, ..., J, and m being the time index;

a second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, ..., J, and m being the time index;

a first time-frequency segment division unit for dividing said time-frequency sub-band representation $s_j(m)$ of the noise-free versions of the target signal into time-frequency segments $S_m$ corresponding to a number N of successive samples of said sub-band signals;

a second time-frequency segment division unit for dividing said time-frequency sub-band representation $x_j(m)$ of the noisy and/or processed version x of the target signal into time-frequency segments $X_m$ corresponding to a number N of successive samples of said sub-band signals;

a normalization and transformation unit configured to provide at least one normalization and/or transformation operation of rows and at least one normalization and/or transformation operation of columns of the time-frequency segments $S_m$ and $X_m$;

an intermediate speech intelligibility calculation unit configured to provide intermediate speech intelligibility coefficients $d_m$ estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$; and a final monaural speech intelligibility calculation unit for calculating the final monaural speech intelligibility predictor d estimating an intelligibility of said noisy and/or processed version x of the target signal by combining, e.g. by averaging, or by applying a MIN or MAX-function to, said intermediate speech intelligibility coefficients $d_m$, or a transformed version thereof, over time, wherein the intermediate speech intelligibility calculation unit is configured to determine said intermediate speech intelligibility coefficients $d_m$ in dependence on a, e.g. linear, sample correlation coefficient d(a,b) of the elements in two K×1 vectors a and b, d(a,b) being defined by:

$$d(a,b) = \frac{\sum_{k=1}^{K}(a(k)-\mu_a)(b(k)-\mu_b)}{\sqrt{\sum_{k=1}^{K}(a(k)-\mu_a)^2(b(k)-\mu_b)^2}},$$

where $\mu_a = \frac{1}{K}\sum_{k=1}^{K}a(k)$ and $\mu_b = \frac{1}{K}\sum_{k=1}^{K}b(k),$ where k is the index of the vector entry and K is the vector dimension, and wherein the intermediate intelligibility index $d_m$ is defined as the average sample correlation coefficient of all columns in $S_m$ and $X_m$, or $\tilde{S}_m$ and $\tilde{X}_m$, respectively, i.e., $$d_m = \frac{1}{N}\sum_{n=1}^{N} d(\tilde{S}_m(:,n), \tilde{X}_m(:,n)),$$

n being a column index, or as
the average sample correlation coefficient of all rows in $S_m$ and $X_m$, or $\tilde{S}_m$ and $\tilde{X}_m$, i.e., $$d_m = \frac{1}{J}\sum_{j=1}^{J} d(\tilde{S}_m(j,:)^T, \tilde{X}_m(j,:)^T),$$

j being a row index, or as
the sample correlation coefficient of all elements in $S_m$ and $X_m$, or $\tilde{S}_m$ and $\tilde{X}_m$, i.e., $$d_m = d(\tilde{S}_m(:), \tilde{X}_m(:)),$$

where the notation $S_m(:)$ and $X_m(:)$, or $\tilde{S}_m(:)$ and $\tilde{X}_m(:)$, represents NJ×1 vectors formed by stacking the columns of the respective matrices.

12. A monaural speech intelligibility predictor unit according to claim 1 wherein the final speech intelligibility calculation unit is configured to calculate the final speech intelligibility predictor d from the intermediate speech intelligibility coefficients $d_m$, optionally transformed by a function $u(d_m)$, as an average over time of said information signal x:

$$d = \frac{1}{M}\sum_{m=1}^{M} u(d_m)$$

where M represents the duration in time units of the speech active parts of said noisy and/or processed version x of the target signal.

13. A monaural speech intelligibility predictor unit configured to receive a target signal comprising speech in a noise-free version s and in a noisy and/or processed version x, the monaural speech intelligibility predictor unit being further configured to provide as an output a final monaural speech intelligibility predictor value d indicative of a listener's perception of said noisy and/or processed version x of the target signal, the monaural speech intelligibility predictor unit comprising:
- a first input unit for providing a time-frequency representation s(k,m) of said noise-free version s of the target signal, k being a frequency bin index, k=1, 2, ..., K, and m being a time index;
- a second input unit for providing a time-frequency representation x(k,m) of said noisy and/or processed version x of the target signal, k being a frequency bin index, k=1, 2, ..., K, and m being a time index;
- a first envelope extraction unit for providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, ..., J, and m being the time index;
- a second envelope extraction unit for providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, ..., J, and m being the time index;
- a first time-frequency segment division unit for dividing said time-frequency sub-band representation $s_j(m)$ of the noise-free version s of the target signal into time-frequency segments $S_m$ corresponding to a number N of successive samples of said sub-band signals;
- a second time-frequency segment division unit for dividing said time-frequency sub-band representation $x_j(m)$ of the noisy and/or processed version x of the target signal into time-frequency segments $X_m$ corresponding to a number N of successive samples of said sub-band signals;
- a normalization and transformation unit configured to provide at least one normalization and/or transformation operation of rows and at least one normalization and/or transformation operation of columns of the time-frequency segments $S_m$ and $X_m$;
- an intermediate speech intelligibility calculation unit configured to provide intermediate speech intelligibility coefficients $d_m$ estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$;
- a final monaural speech intelligibility calculation unit for calculating the final monaural speech intelligibility predictor d estimating an intelligibility of said noisy and/or processed version x of the target signal by combining, e.g. by averaging, or by applying a MIN or MAX-function to said intermediate speech intelligibility coefficients $d_m$, or a transformed version thereof, over time,
- 1 wherein the final speech intelligibility calculation unit is configured to calculate the final speech intelligibility predictor d from the intermediate speech intelligibility coefficients $d_m$, optionally transformed by a function $u(D_m)$, as an average over time of said information signal x:

$$d = \frac{1}{M}\sum_{m=1}^{M} u(d_m)$$

where represents the duration in time units of the speech active parts of said noisy and/or processed version x of the target signal, and
wherein the function $u(d_m)$ is defined as $$u(d_m) = \log\left(\frac{1}{1-d_m^2}\right),$$

or as $$u(d_m) = d_m.$$

14. A hearing aid configured to be located at or in left or right ears of a user, or for being fully or partially implanted in the head of the user, the hearing aid comprising a monaural speech intelligibility predictor unit according to claim 1.

15. A hearing aid according to claim 14 configured to adaptively modify the processing of an input signal to the hearing aid to maximize the monaural speech intelligibility predictor d, to enhance the user's intelligibility of an output signal of the hearing aid presented to the user.

16. A binaural hearing system comprising left and right hearing aids according to claim 14, wherein each of the left and right hearing aids comprises antenna and transceiver circuitry for allowing a communication link to be established and information to be exchanged between said left and right hearing aids, the binaural hearing system further comprising a binaural speech intelligibility prediction unit for providing a final binaural speech intelligibility measure $d_{binaural}$ of the predicted speech intelligibility of the user, when exposed to said sound input, based on monaural speech intelligibility predictor values $d_{left}$, $d_{right}$ of the respective left and right hearing aids.

17. A binaural hearing system according to claim 16, wherein the respective configurable signal processors of the left and right hearing aids are configured to control or influence the processing of the respective electric input signals to maximize said final binaural speech intelligibility measure $d_{binaural}$.

18. A method of providing a monaural speech intelligibility predictor for estimating a user's ability to understand an information signal x comprising a noisy and/or processed version of a target speech signal, the method comprising
- providing a time-frequency representation s(k,m) of a noise-free versions of the target signal, k being a frequency bin index, k=1, 2, ..., K, and m being a time index;

providing a time-frequency representation x(k,m) of said noisy and/or processed version x of the target signal, k being a frequency bin index, k=1, 2, ..., K, and m being a time index;

providing a time-frequency sub-band representation $s_j(m)$ of the noise-free version s of the target signal representing temporal envelopes, or functions thereof, of frequency sub-band signals $s_j(m)$ of said noise-free target signal, j being a frequency sub-band index, j=1, 2, ..., J, and m being the time index;

providing a time-frequency sub-band representation $x_j(m)$ of the noisy and/or processed version x of the target signal representing temporal envelopes, or functions thereof, of frequency sub-band signals $x_j(m)$ of said noisy and/or processed version of the target signal, j=1, 2, ..., J, and m being the time index;

dividing said time-frequency sub-band representation $s_j(m)$ of the noise-free version s of the target signal into time-frequency segments $S_m$ corresponding to a number N of successive samples of said sub-band signals;

dividing said time-frequency sub-band representation $x_j(m)$ of the noisy and/or processed version x of the target signal into time-frequency segments $X_m$ corresponding to a number N of successive samples of said sub-band signals;

providing at least one normalization and/or transformation operation of rows and at least one normalization and/or transformation operation of columns of the time-frequency segments $S_m$ and $X_m$;

providing intermediate speech intelligibility coefficients estimating an intelligibility of said time-frequency segment $X_m$, said intermediate speech intelligibility coefficients $d_m$ being based on said noise-free, normalized and/or transformed time frequency segments $\tilde{S}_m$, and said noisy and/or processed, normalized and/or transformed time-frequency segments $\tilde{X}_m$;

calculating a final monaural speech intelligibility predictor d estimating an intelligibility of said noisy and/or processed version x of the target signal by combining, e.g. by averaging or applying a MIN or MAX-function, said intermediate speech intelligibility coefficients $d_m$, or a transformed version thereof, over time, wherein said first and second time-frequency segment division units are configured to divide said time-frequency representations $s_j(m)$ and $x_j(m)$, respectively, into segments in the form of spectrograms corresponding to N successive samples of all sub-band signals, wherein the $m^{th}$ segment is defined by the J×N matrix $$Z_m = \begin{bmatrix} z_1(m-N+1) & \ldots & z_1(m) \\ \ldots & \ldots & \ldots \\ z_j(m-B+1) & \ldots & z_j(m) \end{bmatrix},$$

where z (Z) represents s (S) or x (X).

19. A non-transitory computer-readable medium storing a computer program comprising instructions which, when executed by a computer, cause the computer to carry out the method of claim 18.

* * * * *